United States Patent
Tragl et al.

(10) Patent No.: US 10,411,170 B2
(45) Date of Patent: Sep. 10, 2019

(54) RADIATION-EMITTING OPTOELECTRONIC DEVICE

(71) Applicant: OSRAM Opto Semiconductors GmbH, Regensburg (DE)

(72) Inventors: Sonja Tragl, Augsburg (DE); Dominik Eisert, Regensburg (DE); Stefan Lange, Augsburg (DE); Nils Kaufmann, Regensburg (DE); Alexander Martin, Regensburg (DE); Krister Bergenek, Regensburg (DE)

(73) Assignee: OSRAM OPTO SEMICONDUCTORS GMBH, Regensburg (DE)

( * ) Notice: Subject to any disclaimer, the term of this patent is extended or adjusted under 35 U.S.C. 154(b) by 0 days.

(21) Appl. No.: 15/570,699

(22) PCT Filed: Apr. 29, 2016

(86) PCT No.: PCT/EP2016/059672
§ 371 (c)(1),
(2) Date: Oct. 30, 2017

(87) PCT Pub. No.: WO2016/174236
PCT Pub. Date: Nov. 3, 2016

(65) Prior Publication Data
US 2018/0358514 A1 Dec. 13, 2018

(30) Foreign Application Priority Data
Apr. 30, 2015 (DE) .................. 10 2015 106 757

(51) Int. Cl.
*H01L 33/50* (2010.01)
*C09K 11/77* (2006.01)
(Continued)

(52) U.S. Cl.
CPC .......... *H01L 33/502* (2013.01); *A61B 1/0653* (2013.01); *A61B 1/0661* (2013.01);
(Continued)

(58) Field of Classification Search
CPC .......... H01L 33/50–508; H01L 33/502; H01L 33/505; H01L 33/62; H01L 33/486;
(Continued)

(56) References Cited

U.S. PATENT DOCUMENTS 8,323,528 B1 * 12/2012 Jia ..................... C09K 11/7769
252/301.4 F
8,405,111 B2 3/2013 Fuchi et al.
(Continued)

FOREIGN PATENT DOCUMENTS

DE 102006013055 A1 9/2007
DE 102012112751 A1 6/2014
(Continued)

OTHER PUBLICATIONS

"Cr3+-Doped Lanthanum Gallogermanate Phosphors with Long Persistent IR Emission" by D. Jia, L. A. Lewis, and Xiao-jun Wang, in Electrochemical and Solid-State Letters, 13 (4) J32-J34 (2010) (Year: 2010).*

(Continued)

*Primary Examiner* — Eric A. Ward
(74) *Attorney, Agent, or Firm* — Slater Matsil, LLP

(57) ABSTRACT

A radiation-emitting optoelectronic device, a method for using a radiation-emitting optoelectronic device and a method for making a radiation-emitting optoelectronic device are disclosed. In an embodiment, the device includes a semiconductor chip configured to emit a primary radiation and a conversion element including a conversion material which comprises Cr and/or Ni ions and a host material and which, during operation of the device, converts the primary (Continued)

radiation emitted by the semiconductor chip into a secondary radiation of a wavelength between 700 nm and 2000 nm, wherein the host material comprises $EAGa_{12}O_{19}$, $A_yGa_5O_{(15+y)/2}$, $AE_3Ga_2O_{14}$, $Ln_3Ga_5GeO_{14}$, $Ga_2O_3$, $Ln_3Ga_{5.5}D_{0.5}O_{14}$ or $Mg_4D_2O_9$, wherein EA=Mg, Ca, Sr and/or Ba, A=Li, Na, K and/or Rb, AE=Mg, Ca, Sr and/or Ba, Ln=La, Ce, Pr, Nd, Pm, Sm, Eu, Gd, Tb, Dy, Ho, Er, Tm, Yb and/or Lu and D=Nb and/or Ta, and wherein y=0.9-1.9.

16 Claims, 11 Drawing Sheets

(51) Int. Cl.
*A61B 1/06* (2006.01)
*H01L 33/48* (2010.01)
*H01L 33/58* (2010.01)
*H01L 33/62* (2010.01)

(52) U.S. Cl.
CPC ............ *C09K 11/77* (2013.01); *H01L 33/50* (2013.01); *H01L 33/505* (2013.01); *H01L 33/486* (2013.01); *H01L 33/58* (2013.01); *H01L 33/62* (2013.01); *H01L 2224/48091* (2013.01); *H01L 2224/48247* (2013.01); *H01L 2224/48472* (2013.01); *H01L 2224/73265* (2013.01); *H01L 2224/8592* (2013.01); *H01L 2924/181* (2013.01); *H01L 2933/0041* (2013.01)

(58) Field of Classification Search
CPC ........... H01L 33/58; H01L 2224/48091; H01L 2224/48247; H01L 2224/48472; H01L 2224/73265; H01L 2224/8592; H01L 2924/181; H01L 2933/041; A61B 1/0653; A61B 1/0661; A61B 1/0684; C09K 11/00–07; C09K 11/08–897; C09K 11/60; C09K 11/607; C09K 11/77
See application file for complete search history.

(56) References Cited

U.S. PATENT DOCUMENTS

| | | | | |
|---|---|---|---|---|
| 8,426,871 B2* | 4/2013 | Rapoport | ................ | H01L 33/50 257/79 |
| 8,758,646 B2* | 6/2014 | Jia | ........................ | C09K 11/681 252/301.36 |
| 8,877,096 B2* | 11/2014 | Pan | ........................ | C04B 35/01 252/301.36 |
| 9,859,473 B2 | 1/2018 | Göötz et al. | | |
| 2006/0069314 A1* | 3/2006 | Farr | ................... | A61B 1/00096 600/179 |
| 2008/0121911 A1 | 5/2008 | Andrews et al. | | |
| 2009/0242839 A1 | 10/2009 | Winkler et al. | | |
| 2011/0260194 A1 | 10/2011 | Fuchi et al. | | |
| 2012/0261617 A1 | 10/2012 | Pan et al. | | |

FOREIGN PATENT DOCUMENTS

| | | |
|---|---|---|
| DE | 102013106573 A1 | 12/2014 |
| EP | 2380944 A1 | 10/2011 |
| EP | 2595206 A1 | 5/2013 |
| JP | 2011188001 A | 9/2011 |
| WO | 2009134507 A2 | 11/2009 |
| WO | 2010055831 A | 5/2010 |
| WO | 2011035292 A2 | 3/2011 |

OTHER PUBLICATIONS

"New spectroscopic results of trivalent chromium in magnesium gallate" by L.P. Sosman et al., Journal of Physics and Chemistry of Solids 68 (2007) 22-25 (Year: 2007).*
"Intense Infrared Luminescence in Transparent Glass-Ceramics Containing β-Ga2O3:Ni2+ Nanocrystals" by Shifeng Zhou, Gaofeng Feng, Botao Wu, Nan Jiang, Shiqing Xu, and Jianrong Qiu in J. Phys. Chem. C 2007, 111, 7335-7338 (Year: 2007).*
"Luminescence from LiGa5O8:Cr3+ with Varying Concentrations of Chromium" by B.D. MacCraith et al., Journal of Luminescence 24/25 (1981) 269-272 (Year: 1981).*
Blasse, G. et al., "Luminescent Materials," Springer Verlag, Berlin, 1994, 9 pages.
Zhang, Y. et al., "A Brief Review on Red to Near-Infrared Persistent Luminescence in Transition-Metal-Activated Phosphors," Optical Materials, vol. 36, No. 11, Sep. 1, 2014, 6 pages.

* cited by examiner

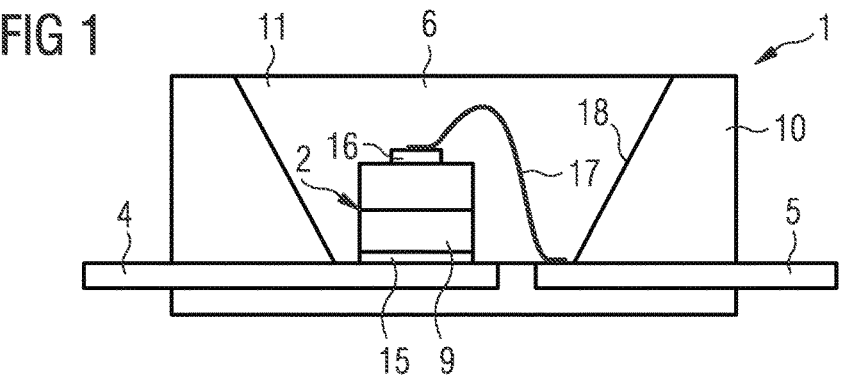
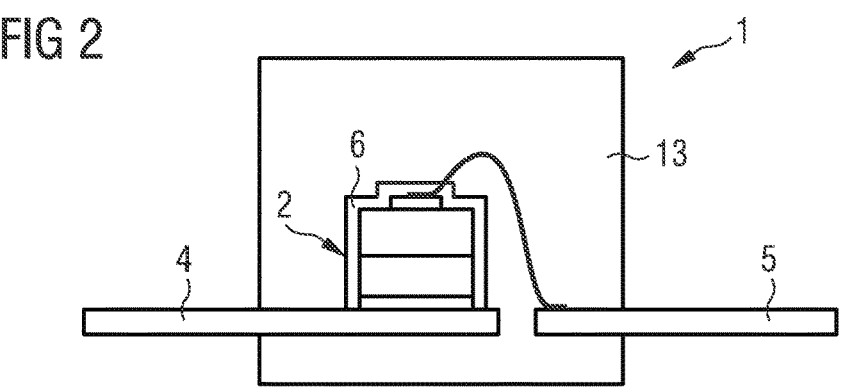
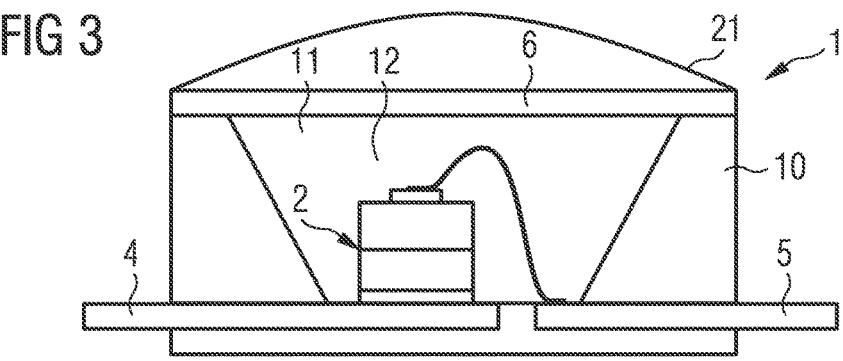
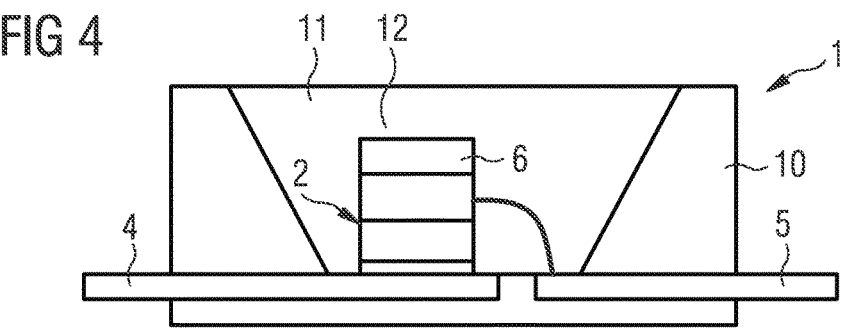

RADIATION-EMITTING OPTOELECTRONIC DEVICE

This patent application is a national phase filing under section 371 of PCT/EP2016/059672, filed Apr. 29, 2016, which claims the priority of German patent application 10 2015 106 757.9, filed Apr. 30, 2015, each of which is incorporated herein by reference in its entirety.

TECHNICAL FIELD

The invention relates to a radiation-emitting optoelectronic device, comprising a conversion element, a use of a radiation-emitting optoelectronic device in a spectrometer and in an endoscope, and relates to a method of producing a radiation-emitting optoelectronic device comprising a conversion element.

BACKGROUND

An established method of analyzing the composition of organic substances, e.g., foodstuffs or polymers, is to record the reflection or transmission of infrared or near-infrared radiation. Infrared radiation or near-infrared radiation excites vibration modes in the material to be examined, which results in characteristic absorption bands. In order to be able to use the complete bandwidth of the near-infrared radiation, light sources having a broad continuous emission spectrum in the desired spectral range are required. The demand for a small, handy and portable analytical apparatus/spectrometer is considerable specifically for analysis carried out by end users, for which reason a small light source is also required. A compact, broadband infrared light source is also required for sensor applications in portable apparatuses and industrial machines. Particularly for applications in the near-infrared range, light sources having a broad continuous emission spectrum are required because this spectral range can be covered by a silicon detector which can be produced in a favorable manner.

Tungsten halogen lamps were hitherto frequently used for the near-infrared range. These lamps are inexpensive and provide a continuous emission with a high intensity in the near-infrared range. However, tungsten halogen lamps have numerous properties which make them disadvantageous for small, handy and portable spectrometers. For example, they generate a great deal of heat, which makes them unattractive for portable spectrometers and the emission wavelength changes over time so that tungsten halogen lamps have only a short service life in comparison with, e.g., LEDs. On the other hand, a certain proportion of emitted radiation is outside the desired wavelength range, as a result of which this energy is lost. Furthermore, they require a considerable volume by reason of the glass casing.

Laser diodes are also used for analyzing materials. In this case, the emission wavelength of the laser diode is selected according to a specific absorption band of the material. Therefore, this method can be used to detect only one component and therefore spectrometers comprising laser diodes can be used only for detecting known substances, such as, e.g., water, carbon dioxide or volatile organic substances. If unknown substances or mixtures are to be analyzed, a broad emission spectrum of the light source is required.

In principle, it is possible to use semiconductor chips which emit radiation in the infrared range. Since previous LEDs which emit radiation in the infrared range have only a very narrow emission width, typically below 50 nm, and since the spectrum typically extends in a peak-like manner, slight changes in the emission wavelength, e.g., as a result of temperature effects, also already have a significant influence upon the intensity of a given wavelength position. In order to cover broader wavelength ranges, a plurality of infrared LEDs would have to be used which must be activated electronically in an individual manner in order to be able to counteract changes in the wavelength of the emission bands and the intensity at elevated temperatures. Moreover, optical elements would be required in order to achieve a mixture of the emission of the radiation of the different LEDs.

Previous light sources frequently have a broadband spectrum with an excessively abrupt or steep change in the intensity or with a strong variation of the spectrum during a sensor measurement or over the service life of the sensor and therefore it is not possible to provide a reliable sensor measurement. Therefore, such light sources are not suitable for precisely analyzing and determining a spectral fingerprint.

Known materials such as Cd (Te,Se) material systems, e.g., quantum dots, satisfy the required criteria of a broad and continuous emission spectrum in the near-infrared range, but they are not suitable for an industrial application owing to the toxicity of cadmium.

Infrared light sources are also used in endoscopes. In conventional endoscopes, 300 W-xenon lamps are used with a filter in order to obtain infrared radiation with a peak wavelength of 785 nm+/−20 nm. A disadvantage of this solution is the considerable losses through the filter and significant heat development and rapid aging of the lamp. Moreover, after being switched on the xenon lamp cannot operate immediately at full radiant power, resulting in waiting times before the endoscope can be used.

SUMMARY OF THE INVENTION

Embodiments of the present invention provide a radiation-emitting optoelectronic device comprising a conversion element having a broad and continuous emission spectrum in the near-infrared range. Further embodiments provide a method for using a radiation-emitting optoelectronic device in a spectrometer or in an endoscope. Yet other embodiments provide a cost-effective and efficient method of producing a radiation-emitting optoelectronic device.

In various embodiments a radiation-emitting optoelectronic device is provided. Said device comprises a semiconductor chip which emits a primary radiation during operation of the device, and comprises a conversion element comprising a conversion material. In particular, the conversion element is arranged in the beam path of the primary radiation of the semiconductor chip.

According to at least one embodiment, the radiation-emitting optoelectronic device comprises two or a plurality of semiconductor chips which emit a primary radiation during operation of the device. The spacing between the semiconductor chips can be between 50 µm and 250 µm from chip edge to chip edge.

According to one embodiment, during operation of the device, the conversion element converts the primary radiation emitted by the semiconductor chip into a secondary radiation in the near-infrared range. Preferably, the secondary radiation has a wavelength between 700 nm and 2000 nm, in particular between 700 nm and 1100 nm. In particular, the wavelength can also be below 1000 nm, i.e., between 700 and 1000 nm.

In one embodiment, the intensity of the secondary radiation is in a region of at least 100 nm at over 20% of the maximum intensity of the secondary radiation. Therefore, the secondary radiation is a broadband radiation. Therefore, a broad emission spectrum can be achieved in the near-infrared spectral range by the device. Preferably, the intensity of the secondary radiation is in a region of at least 150 nm, particularly preferably of at least 200 nm, particularly more preferably of at least 250 nm at over 20% of the maximum intensity of the secondary radiation. Such a broad emission spectrum makes it possible, e.g., to analyze unknown substances or mixtures by means of a spectrometer which comprises the radiation-emitting optoelectronic device.

In one embodiment, the intensity of the secondary radiation is in a region of at least 100 nm at over 30% of the maximum intensity of the secondary radiation. Therefore, the secondary radiation is a broadband radiation. Therefore, a broad emission spectrum can be achieved in the near-infrared spectral range by the device. Preferably, the intensity of the secondary radiation is in a region of at least 150 nm, particularly preferably of at least 200 nm, more particularly preferably of at least 250 nm at over 30% of the maximum intensity of the secondary radiation.

In one embodiment, the intensity of the secondary radiation varies in a region of at least 40 nm, preferably in a region of at least 60 nm, particularly preferably in a region of at least 80 nm and more particularly preferably in a region of at least 100 nm and not more than 5 percent per nm, preferably not more than 3 percent per nm, particularly preferably not more than 2 percent per nm. For example, the intensity in said regions can vary by a maximum of 0.1 to 5 percent per nm, preferably by a maximum of 0.1 to 3 percent per nm, particularly preferably by a maximum of 0.1 to 2 percent per nm. Overall, it is possible to ensure that the intensity per nanometer remains sufficiently homogeneous over a broad spectral range which is relevant, e.g., for the sensor system so that a sensor can detect a spectral fingerprint reproducibly and reliably over the service life. Therefore, it is possible to ensure that a suitable and stable signal reaches the sensor.

According to one embodiment, the conversion material comprises Cr and/or Ni ions and a host material, preferably $Cr^{3+}$ and/or $Ni^{2+}$ ions and a host material. In comparison with cadmium-containing quantum dots, the conversion materials in accordance with the invention have a much lower toxicity, for which reason an industrial application of the radiation-emitting optoelectronic device is possible.

The conversion element is configured for converting, during operation of the device, the primary radiation emitted by the semiconductor chip into a secondary radiation in the near-infrared range. Preferably, the secondary radiation has a wavelength between 700 nm and 2000 nm, in particular between 700 nm and 1100 nm. In particular, the wavelength can also be below 1000 nm, i.e., between 700 and 1000 nm. The wavelength can be in particular the peak wavelength. In the present case, "peak wavelength" defines the wavelength of a peak at which the intensity of the peak is at a maximum.

In comparison with tungsten halogen lamps, the radiation-emitting optoelectronic device has a longer service life and much smaller spatial dimensions can be achieved. Halogen lamps for IR applications typically have a diameter of 20 mm and a length of 101 mm. Therefore, the radiation-emitting optoelectronic device is suitable for use in a small, handy and portable spectrometer.

In one embodiment, the host material is selected from a group of compounds which comprises metal oxides, metal halides, metal nitrides, metal oxynitrides and combinations thereof. Preferably, the host material is a metal oxide.

The semiconductor chip comprises an active epitaxial layer sequence which is suitable for emitting a primary radiation during operation of the radiation-emitting optoelectronic device. According to one embodiment, the semiconductor chip emits a primary radiation in the blue, green or red spectral range. Preferably, the semiconductor chip emits a primary radiation in the blue or red spectral range. In the red and blue spectral range, the conversion material can be excited in a particularly efficient manner.

In order to generate the primary radiation, the epitaxial layer sequence can have, e.g., a pn-junction, a double heterostructure, a single quantum well structure or, particularly preferably, a multiple quantum well structure. The designation "quantum well structure" does not include any indication relating to dimensionality. It thus includes inter alia quantum troughs, quantum wires and quantum dots and any combination of these structures.

A semiconductor chip which is suitable for emitting, during operation, blue primary radiation of a wavelength between 400 and 500 nm is based, e.g., on gallium nitride or indium gallium nitride. In particular, in the application in an endoscope, the dominant wavelength of the primary radiation is preferably between 440 nm and 460 nm.

The dominant wavelength is the monochromatic wavelength which generates the same color impression as a polychromatic light source. In the CIE color diagram, the line connecting a point for a specific color and the point for the color of a light source can be extrapolated such that it meets the contour of the space in a maximum of two points. The point of intersection which is closer to the stated color represents the dominant wavelength of the color as the wavelength of the pure spectral color at this point of intersection. The dominant wavelength is thus the wavelength perceived by the human eye. In general, the dominant wavelength deviates from a wavelength of maximum intensity. In particular, the dominant wavelength is in the red spectral range at smaller wavelengths than the wavelength of maximum intensity.

A semiconductor chip which is suitable for emitting, during operation, red primary radiation of a wavelength between 580 and 700 nm is based, e.g., on gallium arsenide phosphide or aluminum indium gallium phosphide. In particular, in the application in an endoscope the dominant wavelength of the primary radiation is preferably between 615 nm and 650 nm, particularly preferably over 630 nm. The excitation of the conversion material by red primary radiation causes fewer Stokes' losses than in the case of excitation by blue primary radiation, whereby less heat is developed, thus prolonging the service life of the device.

According to one embodiment, the semiconductor chip(s) is/are applied on a circuit board, e.g., a metal core circuit board, AlN or a layer structure of AlN and metal.

According to one embodiment, the semiconductor chip(s) is/are surface-mountable and applied on a substrate based on a ceramic or a lead frame. The term "surface-mountable" means here and hereinafter that the semiconductor chip does not have any wire connections but rather is soldered directly onto a substrate, e.g., a printed circuit board, via solderable connection surfaces. With this arrangement it is possible to arrange many semiconductor chips closely next to one another on a small surface. Therefore, in an advantageous manner a large amount of radiation can be generated on a small surface, which is advantageous in particular in the application in endoscopes. In particular, one semiconductor chip or a plurality of semiconductor chips is/are used which emit radiation only from one surface, so-called surface-emitting semiconductor chips. In comparison with volume-emitting semiconductor chips which emit radiation from 5 surfaces, surface-emitting semiconductor chips achieve a higher luminous density which is advantageous particularly in the case of endoscopes. Examples of surface-emitting semiconductor chips are ThinGaN, Thinfilm or UX3.

In one embodiment, the conversion material converts preferably over 20%, particularly preferably over 40%, more particularly preferably over 50% of the primary radiation into secondary radiation. It is also possible for the conversion material to convert over 90% or over 95% of the primary radiation into secondary radiation.

It is possible for primary radiation, i.e., radiation in the blue or red spectral range, also to be emitted outwards into the area surrounding the radiation-emitting optoelectronic device. This proves to be advantageous if precision localization is to take place relating to the point in the surrounding area at which the radiation in the near-infrared range is to impinge. For example, when using the device in a spectrometer it is thus possible to focus with precision the region of the sample to be analyzed. Even when said device is used in an endoscope the tissue to be treated, e.g., a tumor, can be localized with precision.

In one embodiment, a filter is arranged over the conversion element. In this way, it is possible to prevent primary radiation from being emitted to the surrounding area if this is undesirable. For example, the filter which is used can be a material which absorbs blue, green or red primary radiation but is permeable for the secondary radiation. For example, Schott glass filters can be used but it is also possible to use other filters which are known to the person skilled in the art. It is also possible to use dielectric mirrors which selectively reflect blue, green or red primary radiation. This can be arranged, e.g., on a cover disk. The cover disk can have a wavelength-dependent transmission. For example, the cover disk comprises a glass or consists of glass.

The fact that a layer or an element is arranged or applied "on" or "over" another layer or another element may here and hereinafter mean that the one layer or the one element is arranged in direct mechanical and/or electrical contact with the other layer or the other element. It may moreover also mean that the one layer or the one element is arranged indirectly on or over the other layer or the other element. In this case, further layers and/or elements or a clearance may be arranged between the one layer or the other layer or between the one element or the other element.

For example, the radiation-emitting optoelectronic device can be a light-emitting diode, or LED for short. In other words, the device then emits incoherent radiation during operation. The LED can be designed as a surface-mounted device.

In one embodiment, the Cr and/or Ni ions, preferably $Cr^{3+}$ and/or $Ni^{2+}$ ions partially replace the metals of the host material. This means that the Cr and/or Ni ions, preferably $Cr^{3+}$ and/or $Ni^{2+}$ ions occupy in part the lattice sites of the metals of the host material.

In one embodiment, the Cr and/or Ni ions, preferably $Cr^{3+}$ and/or the $Ni^{2+}$ ions replace 0.01 to 10 mol %, preferably 0.1 to 5 mol %, particularly preferably 0.3 to 3 mol %, e.g., 0, 5 or 1.0 mol % of a metal of the host material. Such a high concentration of Cr and/or Ni ions, preferably $Cr^{3+}$ and/or the $Ni^{2+}$ ions improve the absorption and thus the conversion degree. As a result, a higher radiated power is achieved in the near-infrared range.

In one embodiment, the conversion material does not have any defects or has only very few defects. Defects are understood primarily to be unoccupied lattice sites and foreign ions in the host lattice or ions at intermediate lattice sites of the host material. Defects in the host lattice can result in a decrease in the quantum efficiency of a luminescent material or can result in the occurrence of afterglow, that is to say that the decay time of the luminescence is in the millisecond range. If the conversion material does not have any defects or has only very few defects, a short decay time in the microsecond range can be achieved and therefore the afterglow can be substantially avoided. Afterglow is to be understood to mean that the conversion material continues to emit secondary radiation after the current has been switched off, i.e., upon termination of the operation of the device. A long afterglow is desirable, e.g., for applications of materials which emit near-infrared radiation in the fields of medicine, security and in the military, or for labeling purposes. However, afterglow is undesirable specifically with respect to the use in spectrometers.

The emission of $Cr^{3+}$ ions is greatly dependent upon the strength of the ligand field surrounding them. In a strong ligand field, e.g., $Al_2O_3$, the lowest occupiable, energetically excited state is $^2E$ with a spin-forbidden $^2E \rightarrow {}^4A_2$-transition which results in an emission of a narrow emission band at circa 700 nm. By reason of the spin-forbidden transition, these transitions are very slow and afterglow occurs to an increased extent. In accordance with the invention, host materials having a weak ligand field are used so that the first excited state is a $^4T_2$-state, with a spin-allowed transition $^4T_2 \rightarrow {}^4A_2$ which results in a broadband emission at wavelengths over 700 nm. Since this relates to a spin-allowed transition, the transitions are produced very quickly after excitation so that afterglow of the conversion material can be avoided or almost avoided. $Ni^{2+}$ ions often have a multiple band spectrum because the emission transitions are produced from a plurality of excited states. For example, $Mg_{1-x}Ni_xSiO_3$, where x=0.0001-0.1 demonstrates two emission bands at about 850 nm and 1500 nm.

The host material can be crystalline and/or amorphous compounds, i.e., glass-like compounds. Amorphous compounds can be advantageous for achieving a broadband emission. In an amorphous compound, the surrounding area and thus the ligand field around each metal atom and activator ion, such as the Cr and Ni ion is slightly different, whereas in crystalline compounds the number of "surrounding areas" is determined by the number of crystallographic positions available to the activator ions, such as Cr or Ni ions. The position of an emission band is displaced in dependence upon the ligand field so that in the case of amorphous compounds slightly different emission bands are superimposed and therefore the emission spectrum is broadened.

According to one embodiment, the conversion material is $Cr^{3+}$- and/or $Ni^{2+}$-doped silicates, aluminates, gallates, niobates and/or germanates. Oxygen ions and metal ions can be arranged in these host materials in such a way that if anything weak interactions occur between the d orbital of a central metal ion and the surrounding oxygen ions. Activator ions such as $Cr^{3+}$ or $Ni^{2+}$ which partially replace the metal atoms are then surrounded by a so-called weak ligand field, which favors a broadband emission. By using such a conversion material, the optoelectronic device provides a broad continuous emission spectrum in the near-infrared spectral range. A continuous emission spectrum is to be understood to mean that the intensity above the emitted wavelength range does not abruptly fall or rise, that is to say that the intensity varies by no more than 0.1 to 5 percent per nm. Moreover, the broad continuous emission spectrum can be maintained over the service life of the device, e.g., over a period of 5 to 1000 hours.

In one embodiment, the host material is selected from a group of compounds which comprises $EAGa_{12}O_{19}$, $MgSiO_3$, $A_yGa_5O_{(15+y)/2}$, $AE_3Ga_2Ge_4O_{14}$, $Ln_3Ga_5GeO_{14}$, $Ln_3Ga_{5.5}D_{0.5}O_{14}$, $Ga_2O_3$ and $Mg_4D_2O_9$, where EA=Mg, Ca, Sr and/or Ba, A=Li, Na, K and/or Rb, AE=Mg, Ca, Sr and/or Ba, Ln=La, Ce, Pr, Nd, Pm, Sm, Eu, Gd, Tb, Dy, Ho, Er, Tm, Yb and/or Lu and D=Nb and/or Ta. It is preferable that EA=Sr and/or Ba, A=Na and/or K, AE=Ca and/or Sr, Ln=La and D=Nb. It is also possible for the host material to be a compound which has small deviations in the empirical formulae $EAGa_{12}O_{19}$, $MgSiO_3$, $A_yGa_5O_{(15+y)/2}$, $AE_3Ga_2Ge_4O_{14}$, $Ln_3Ga_5GeO_{14}$, $Ln_3Ga_{5.5}Nb_{0.5}O_{14}$, $Ga_2O_3$ or $Mg_4D_2O_9$. For example, a small quantity of foreign atoms can be present in the host materials. In particular, the host material can comprise or consist of $Ln_3Ga_5O_{14}$ and $Ga_2O_3$, preferably ß-$Ga_2O_3$.

In one embodiment, the host material comprises $Ln_3Ga_5O_{14}$ and $Ga_2O_3$ or consists of these compounds. In particular, the weight proportion of $Ga_2O_3$ can be between 5 and 20 weight percent in relation to the total weight of $Ln_3Ga_5GeO_{14}$ and $Ga_2O_3$.

In one embodiment, the conversion material is selected from a group of compounds which comprises $Mg_{1-x}Ni_xSiO_3$, $A_y(Ga_{1-x}Ni_x)_5O_{[(15+y)/2]-2.5x}$, $AE_3(Ga_{1-x}Ni_x)_2Ge_4O_{14-x}$, $Ln_3(Ga_{1-x}Ni_x)_5GeO_{(28-5x)/2}$, $(Ga_{1-x}Ni_x)_2O_{3-x}$, $Ln_6(Ga_{1-x}Ni_x)_{11}DO_{28-5.5x}$, $(Mg_{1-x}Ni_x)_4D_2O_9$ and combinations thereof, where x=0.0001-0.1, y=0.9-1.9, A=Li, Na, K and/or Rb, AE=Mg, Ca, Sr and/or Ba, Ln=La, Ce, Pr, Nd, Pm, Sm, Eu, Gd, Tb, Dy, Ho, Er, Tm, Yb and/or Lu and D=Nb and/or Ta. It is preferable that A=Na and/or K, AE=Ca and/or Sr, Ln=La and D=Nb. For example, the conversion material is $Mg_{1-x}Ni_xSiO_3$, where x=0.0001-0.1. Preferably, the conversion material is selected from a group of compounds which comprises $A_y(Ga_{1-x}Ni_x)_5O_{[(15+y)/2]-2.5x}$, $AE_3(Ga_{1-x}Ni_x)_2Ge_4O_{14-x}$, $Ln_3(Ga_{1-x}Ni_x)_5GeO_{(28-5x)/2}$, $Ln_6(Ga_{1-x}Ni_x)_{11}DO_{28-5.5x}$, $(Mg_{1-x}Ni_x)_4D_2O_9$ and combinations thereof. Particularly preferably, the conversion material is selected from a group of compounds which comprises $A_y(Ga_{1-x}Ni_x)_5O_{[(15+y)/2]-2.5}$, $AE_3(Ga_{1-x}Ni_x)_2Ge_4O_{14-x}$, $Ln_3(Ga_{1-x}Ni_x)_5GeO_{(28-5x)/2}$ and combinations thereof. In particular, the conversion material can comprise or consist of $Ln_3(Ga_{1-x}Ni_x)_5GeO_{(28-5x)/2}$ and $(Ga_{1-x}Ni_x)_2O_{3-x}$. Preferably, $(Ga_{1-x}Ni_x)_2O_{3-x}$ is or is produced as a secondary phase.

In one embodiment, the conversion material is selected from a group of compounds which comprises $EA(Ga_{1-x'}Cr_{x'})_{12}O_{19}$, $(Mg_{1-x'}Cr_{x'})Si_{(4-x')/4}O_3$, $A_{y'}(Ga_{1-x'}Cr_{x'})_5O_{(15+y')/2}$, $AE_3(Ga_{1-x'}Cr_{x'})_2Ge_4O_{14}$, $Ln_3(Ga_{1-x'}Cr_{x'})_5GeO_{14}$, $(Ga_{1-x'}Cr_{x'})_2O_3$, $Ln_6(Ga_{1-x'}Cr_{x'})_{11}DO_{28}$, $(Mg_{1-x'}Cr_{x'})_{8/(2-x')}D_2O_9$ and combinations thereof, where x'=0.0001-0.1, y'=0.9-1.9, EA=Mg, Ca, Sr and/or Ba, A=Li, Na, K and/or Rb, AE=Mg, Ca, Sr and/or Ba, Ln=La, Ce, Pr, Nd, Pm, Sm, Eu, Gd, Tb, Dy, Ho, Er, Tm, Yb and/or Lu and D=Nb and/or Ta. It is preferable that A=Na and/or K, AE=Ca and/or Sr, Ln=La and D=Nb. Preferably, the conversion material is selected from a group of compounds which comprises $EA(Ga_{1-x}Cr_{x'})_{12}O_{19}$, $A_{y'}(Ga_{1-x'}Cr_{x'})_5O_{(15+y')/2}$, $AE_3(Ga_{1-x'}Cr_{x'})_2Ge_4O_{14}$, $Ln_3(Ga_{1-x'}Cr_{x'})_5GeO_{14}$, $Ln_6(Ga_{1-x'}Cr_{x'})_{11}DO_{28}$, $(Mg_{1-x'}Cr_{x'})_{8/(2-x')}D_2O_9$ and combinations thereof. Particularly preferably, the conversion material is selected from a group of compounds which comprises $EA(Ga_{1-x'}Cr_{x'})_{12}O_{19}$, $A_{y'}(Ga_{1-x'}Cr_{x'})_5O_{(15+y')/2}$, $AE_3(Ga_{1-x'}Cr_{x'})_2Ge_4O_{14}$, $Ln_3(Ga_{1-x'}Cr_{x'})_5GeO_{14}$ and combinations thereof. For example, the conversion material is $SrGa_{11.88}Cr_{0.12}O_{19}$, $La_3Ga_{4.975}Cr_{0.025}GeO_{14}$, $La_3Ga_{4.95}Cr_{0.05}GeO_{14}$, $Ca_3Ga_{1.98}Cr_{0.02}Ge_4O_{14}$ or $Na_{1.4}Ga_{4.95}Cr_{0.05}O_{8.2}$. In particular, the conversion material can comprise or consist of $Ln_3(Ga_{1-x'}Cr_{x'})_5GeO_{14}$ and $(Ga_{1-x'}Cr_{x'})_2O_3$. Preferably, $(Ga_{1-x'}Cr_{x'})_2O_3$ is or is produced as a secondary phase.

In one embodiment, the conversion material $AE_3(Ga_{1-x'}Cr_{x'})_2Ge_4O_{14}$ contains a secondary phase of Cr-doped gallium oxide $(Ga_{1-x'}Cr_{x'})_2O_3$. The secondary phase, i.e., the Cr-doped $Ga_2O_3$ emits a secondary radiation in the range of 650 nm to 850 nm. In particular, the peak wavelength of the Cr-doped $Ga_2O_3$ is in the range of 700 to 750 nm.

In one embodiment, x and/or x' is independently selectable for each compound. It is preferable that x, x'=0.001-0.05, particularly preferably 0.003-0.025, e.g., 0.005 or 0.01.

In one embodiment, the conversion material can also be a combination of one or a plurality of $Ni^{2+}$-doped compounds and one or a plurality of $Cr^{3+}$-doped compounds.

A combination of conversion materials results in a more uniform distribution of the intensity of the radiation. For example, a combination of the luminescent materials $A_{y'}(Ga_{1-x'}Cr_{x'})_5O_{(15+y')/2}$ and $Ln_3(Ga_{1-x'}Cr_{x'})_5GeO_{14}$ can be used. $Ln_3(Ga_{1-x'}Cr_{x'})_5GeO_{14}$ can contain as a secondary phase $(Ga_{1-x'}Cr_{x'})_2O_3$.

According to at least one embodiment, the conversion material comprises $La_3(Ga_{1-x'}Cr_{x'})_5GeO_{14}$ and $(Ga_{1-x'}Cr_{x'})_2O_3$ or consists of these compounds. The conversion material can be produced from the initial weights of the starting materials corresponding to the empirical formula $La_3(Ga_{1-x'}Cr_{x'})_5GeO_{14}$.

According to one embodiment, the conversion material is a powder. The powder can have converter particles. The converter particles have a particle diameter of 1 to 50 µm, preferably 3 to 20 µm, particularly preferably 5 to 15 µm. The particle size can be determined by laser diffraction methods.

In one embodiment, the conversion material comprises a conversion material and a matrix material or consists of a conversion material and a matrix material. The conversion material can be embedded in the matrix material. For example, converter particles are embedded in the matrix material. It is possible for the conversion material to be distributed homogeneously in the matrix material. However, it is also possible for the conversion material to be distributed with a concentration gradient in the matrix material. In particular, the matrix material has or consists of one of the following materials: a silicone, a polysilazane, an epoxy, a polyurethane, an acrylate, a polycarbonate, a glass, a ceramic. If a semiconductor chip which emits blue radiation is used, a silicone is preferably used because this matrix material is particularly stable with respect to blue radiation, that is to say that it does not become yellow or cloudy over the operating life of the device. If a semiconductor chip which emits red radiation is used, an epoxy is preferably used because this matrix material is particularly cost-effective and has a low permeability with respect to moisture so that the semiconductor chip in this embodiment is protected particularly effectively against moisture, which results in a prolonged service life of the device.

Since the conversion element also produces heat in addition to the secondary radiation, it is particularly advantageous to use a glass having an increased thermal conductivity as the matrix material.

In one possible embodiment, the conversion element is designed in the form of a casting compound, wherein the casting compound encases the semiconductor chip in a form-fitting manner. Furthermore, the casting compound which encases the semiconductor chip in a form-fitting manner can be stabilized on the side walls, e.g., by a housing and is located, e.g., in a recess of such a housing.

In one embodiment, the side walls of the recess are reflective. As a result, it is possible to achieve a more narrow-angled emission and therefore the intensity can be increased in the illumination region, in particular in the region of an emission angle of +/−40° to +/−60°. Therefore, it is possible for the secondary radiation to be emitted in a focused manner outwards. The radiation in the near-infrared range can thus also be directed locally to small objects or small regions, e.g., of an object which is to be examined by a spectrometer which comprises the radiation-emitting optoelectronic device. Therefore, when the device is used in a spectrometer it is possible to focus with precision the region of the sample to be analyzed.

Furthermore, the conversion element can be designed as a conversion layer. In the case of the conversion layer, there is a direct contact between the conversion layer and semiconductor chip, wherein the thickness of the conversion layer, e.g., is less than the thickness of the semiconductor chip and can be, e.g., constant on all radiation exit surfaces. Such a conversion layer is applied in particular by the following methods: spray-coating, injection molding, transfer molding, jetting, dispensing or electrophoresis.

In one embodiment, the conversion material is present at 1-60 weight percent, preferably 5-40 weight percent, particularly preferably 10-40 weight percent in relation to the total mass of conversion material and matrix material.

The conversion element can also take the form of a plate or a film. The plate or film is arranged over the semiconductor chip. In the case of these further variants of the embodiment of the conversion element, there is not necessarily a direct and/or form-fitting contact between the conversion element and the semiconductor chip. That is to say that there can be a spaced interval between the conversion element and the semiconductor chip. In other words, the conversion element is arranged downstream of the semiconductor chip and is illuminated by the primary radiation. A casting compound body or an air gap can then be formed between the conversion element and semiconductor chip. It is advantageous in this geometric arrangement that in particular by reason of the spaced interval between the conversion element and semiconductor chip, the conversion element is heated to a reduced extent by the lost heat from the semiconductor chip. For example, the plate or film comprises or consists of silicone and the conversion material.

According to one embodiment, the conversion element comprises thermally conductive materials. The thermally conductive materials are selected from a group which comprises $Al_2O_3$, AlN, $SiO_2$ and combinations thereof.

Thermally conductive materials do not cause any heat to build up in the conversion element and a constant luminous intensity and a constant color point can be guaranteed throughout the operating life of the optoelectronic device. Therefore, premature failure of the optoelectronic device can be prevented and the service life of the optoelectronic device can be prolonged. In particular, if the quantum efficiency of the conversion material is not very high and heat is produced in addition to the secondary radiation, the addition of thermally conductive materials is advantageous.

According to one embodiment, the conversion element comprises luminescent materials which convert the primary radiation into a second secondary radiation in the blue, green or red range of the electromagnetic spectrum. The second secondary radiation is thus in the visible range and is emitted in addition to the secondary radiation in the near-infrared range outwards into the area surrounding the radiation-emitting optoelectronic device. This proves to be advantageous if precision localization is to take place relating to the point in the surrounding area at which the secondary radiation in the near-infrared range is to impinge. For example, when using the device in a spectrometer it is thus possible to focus with precision the region of the sample to be analyzed.

In one embodiment, the conversion element consists of the conversion material. For example, this can be a ceramic of the conversion material. For example, the embodiment of the conversion element as a plate is a plate consisting of a ceramic of the conversion material. Preferably, the plate has a low porosity. This can prevent or almost prevent undesired light scattering and effective heat dissipation is achieved.

In one embodiment, the device comprises an optical element, e.g., a wavelength-orienting element, such as, e.g., a lens. As a result, it is possible to achieve a more narrow-angled emission and therefore the intensity can be increased in the illumination region, in particular in the region of an emission angle of +/−40° to +/−60°. Therefore, it is possible for the secondary radiation to be emitted in a focused manner outwards. The radiation in the near-infrared range can thus also be directed locally to small objects or small regions, e.g., of an object which is to be examined by a spectrometer which comprises the radiation-emitting optoelectronic device. Therefore, when the device is used in a spectrometer it is possible to focus with precision the region of the sample to be analyzed.

The indicated embodiments of the radiation-emitting optoelectronic device can be deployed for uses stated hereinafter.

A use of the radiation-emitting optoelectronic device according to the above-stated embodiments for sensor applications is provided.

A use of the radiation-emitting optoelectronic device according to the above-stated embodiments in a spectrometer is provided.

By virtue of the fact that the radiation-emitting optoelectronic device in accordance with the invention provides a broad continuous emission spectrum in the near-infrared spectral range, one radiation-emitting optoelectronic device in a spectrometer is sufficient. Therefore, it is possible to provide a spectrometer with only one light source and still obtain an emission in the desired width. Therefore, it is possible to provide a spectrometer which can be easily handled and carried. This can be used in particular on a daily basis by end users.

The spectrometer can be used to analyze organic substances, such as foodstuffs and polymers.

In one embodiment of the use of the radiation-emitting optoelectronic device, the spectrometer comprises a sensor.

In one embodiment, the sensor is a silicon detector. Preferably, this sensor is used if the secondary radiation is at a wavelength between 700 nm and 1100 nm.

In the case of the use of the inventive radiation-emitting optoelectronic device in a spectrometer, it is possible to ensure that the broad and continuous emission spectrum is maintained during the measuring time, i.e., for a duration of about 25 ms to 10 s. In the present case, the measuring time is to be understood to mean the time taken to perform the actual measurement. This means that the measuring time begins as soon as the maximum intensity of the emission of the device is achieved. In particular, the switch-on procedure and the switch-off procedure are not included in the measuring time. The fact that the broad and continuous emission spectrum is maintained during the measuring time means that wavelength-dependent intensity changes do not occur abruptly but instead vary by 1-20% at the most in less than one fifth of the measuring time. Moreover, the broad continuous emission spectrum can be maintained over the service life of the sensor, e.g., over period of 5 to 1000 hours. Overall, it is thus possible to ensure that the intensity per nanometer remains sufficiently homogeneous over a broad spectral range which is relevant for the sensor system so that the sensor can detect a typical spectral fingerprint reproducibly and reliably over the service life. It is thus possible to ensure that a suitable and stable signal reaches the sensor.

The indicated embodiments of the radiation-emitting optoelectronic device can thus be a part of a spectrometer.

A spectrometer is provided, comprising a radiation-emitting optoelectronic device according to one of the above-described embodiments.

In one embodiment, the spectrometer comprises a radiation-emitting optoelectronic device according to one of the above-described embodiments and comprises a sensor.

In one embodiment, the sensor is a silicon detector. Preferably, this sensor is used if the secondary radiation is at a wavelength between 700 nm and 1100 nm. The radiation-emitting optoelectronic device which has a secondary radiation at a wavelength between 700 nm and 1100 nm can be advantageously combined with a silicon detector. Silicon detectors can be produced cost-effectively in comparison with other sensors. Therefore, the spectrometer as a whole can be produced cost-effectively.

In one embodiment, the spectrometer is suitable for installation in a smartphone. This is possible by reason of the small spatial dimensions of the radiation-emitting optoelectronic device. Therefore, it is possible using smartphones, for example, to obtain information relating to the ingredients in foodstuffs, e.g., the sugar content, quickly and reliably.

Therefore, in one embodiment the spectrometer can be included in a smartphone.

A use of the radiation-emitting optoelectronic device according to the above-stated embodiments in an endoscope is provided.

By virtue of the fact that, during operation, the radiation-emitting optoelectronic device in accordance with the invention emits radiation in the near-infrared range, e.g., at a peak wavelength between 780 nm and 790 nm, e.g., 785 nm, it is possible to identify and/or treat, e.g., tumors. The endoscopes are thus suitable for use in photodynamic diagnostics and/or photodynamic therapy. Preferably, the radiation has a full width at half maximum (FWHM) of about 40 nm.

In one embodiment, the endoscopes are suitable for making the distribution of a fluorescent contrast agent, such as, e.g., indocyanine green visible in a tissue so that, e.g., lymphatic vessels or the perfusion of an organ region can be visualized. The near-infrared radiation is thus used as excitation radiation for the fluorescent contrast agent.

In one embodiment, the radiation-emitting optoelectronic device in the endoscope has $SrGa_{11.88}Cr_{0.12}O_{19}$ or $Na_{1.4}Ga_{4.95}Cr_{0.05}O_{8.2}$ as the conversion material.

An endoscope is provided, comprising a radiation-emitting optoelectronic device according to one of the above-described embodiments.

The radiation-emitting optoelectronic device preferably comprises one or a plurality of semiconductor chips, in particular the semiconductor chips emit, during operation, a primary radiation at a dominant wavelength between 615 nm and 650 nm or between 440 nm and 460 nm. The spacing between the semiconductor chips can be between 50 μm and 250 μm from chip edge to chip edge. The conversion element is designed as a plate and consists of or comprises the conversion material and, e.g., silicone, ceramic or glass. Alternatively, the conversion element is sprayed or dispersed as a layer having a layer thickness between 20 and 150 μm onto the semiconductor chip(s). The layer can comprise the conversion material and silicone, polysilazane or glass or can consist of these materials. Therefore, radiation-emitting optoelectronic devices having a high luminous density can be provided. Moreover, it is possible to operate the radiation-emitting optoelectronic devices with high current densities, e.g., with up to 4 A/mm² chip surface area.

According to one embodiment, the endoscope comprises a filter in order to obtain the target wavelength.

The endoscopes are characterized by the fact that the heat development is very low and only small losses are produced during filtering in order to achieve the target wavelength. The dimensions of the endoscope can be minimized through the use of a radiation-emitting device in accordance with the invention which takes up only a small amount of space. Furthermore, the radiation-emitting devices are characterized by a high luminous density, which is very important for use in an endoscope in order to couple as much light as possible into the fiber of the endoscope. In particular, in order to achieve high luminous densities surface-emitting semiconductor chips are used. Moreover, the endoscope can be used directly after being switched on because, in contrast to previously used lamps, no warming-up period is required.

The indicated embodiments of the radiation-emitting optoelectronic device can be produced according to methods indicated hereinafter.

A method of producing a radiation-emitting optoelectronic device is provided. The method comprises the following method steps: A) providing a semiconductor chip which is configured for emitting a primary radiation during operation of the device, B) producing a conversion element, comprising a conversion material which comprises Cr and/or Ni ions and a host material, wherein the host material is selected from a group of compounds which comprises metal oxides, metal halides, metal nitrides, metal oxynitrides and combinations thereof, C) applying the conversion element over the semiconductor chip, wherein the conversion element is configured for converting, during operation of the device, the primary radiation emitted by the semiconductor chip into secondary radiation of a wavelength between 700 nm and 1100 nm.

In comparison with quantum dots, the conversion materials in accordance with the invention can be produced and handled without a protective gas atmosphere or even encasing protective layers, thus permitting industrial, cost-effective production of the radiation-emitting optoelectronic device.

In one embodiment, the conversion material comprises $Cr^{3+}$ and/or $Ni^{2+}$ ions.

In one embodiment, method step B) comprises a method step BB): BB) producing the conversion material.

In one embodiment, method step BB) comprises the following method steps: BB1) mixing the starting materials, BB2) calcining the mixture obtained in BB1) at a temperature between 700° C. and 1500° C.

The starting materials can be mixed in method step BB1), e.g., with the aid of a mixer and/or a mortar mill.

In one embodiment, the calcining in method step BB2) takes place for one to ten hours, preferably one to five hours, e.g., for four hours.

In one embodiment, method step BB1) comprises mixing the starting materials together and dissolving the starting materials in a mineral acid.

In one embodiment, the mineral acid is selected from a group which comprises sulfuric acid, phosphoric acid, hydrochloric acid and nitric acid and combinations thereof.

Dissolving the starting materials in a mineral acid causes the formation of homogeneous mixtures of the starting materials which are partially hydrolyzed to form more reactive starting materials. For example, oxides which are used are hydrolyzed to form hydroxides. Therefore, the reaction time and/or the reaction temperature can be reduced during the calcining in method step BB2).

In one embodiment, method step BB2) is followed by method step BB3): BB3) grinding and sieving the powder obtained in method step BB2). This method step is performed preferably after the powder has cooled to room temperature.

Method step BB3) can be followed by a further method step BB4): BB4) calcining the powder obtained in BB3) at a temperature between 700° C. and 1500° C.

Method step BB4) can be followed by a further method step BB5): BB5) grinding and sieving the powder obtained in method step BB4). This method step is performed preferably after the powder has cooled to room temperature.

In one embodiment, the following method step takes place after method step BB3) or after method step BB5): BB6) sintering the powder obtained in method step BB3) or BB5) to form a ceramic, in particular a plate consisting of the conversion material.

In one embodiment, the sintering in method step BB6) is performed at a temperature between 700 and 1700° C., e.g., 900° C.

In one embodiment, the sintering in method step BB6) takes place for one to fifteen hours, preferably one to eight hours, e.g., for six hours.

In one embodiment, the powder obtained in method step BB3) or BB5) has binding agents added to it prior to the sintering in method step BB6).

In one embodiment, the following method step BB7) takes place after method step BB3) or after method step BB5): BB7) mixing the powder obtained in method step BB3) or BB5) with a matrix material.

In one embodiment, the starting materials in method step BB1) are selected from a group which comprises metal oxides, metal hydroxides, metal carbonates, metal nitrates, metal halides, metal acetates, metal nitrides and combinations thereof. Preferably, the starting materials are selected from a group which comprises metal oxides, metal hydroxides, metal carbonates and combinations thereof.

In one embodiment, a fluxing agent is added to the starting materials in method step BB1). This can be, e.g., boric acid. This addition improves the reactivity and crystal growth.

BRIEF DESCRIPTION OF THE DRAWINGS

Further advantageous embodiments and developments of the invention are apparent from the exemplified embodiments described below in conjunction with the figures.

FIGS. 1 to 4 show schematic side views of different embodiments of radiation-emitting optoelectronic devices.

Figure 5:
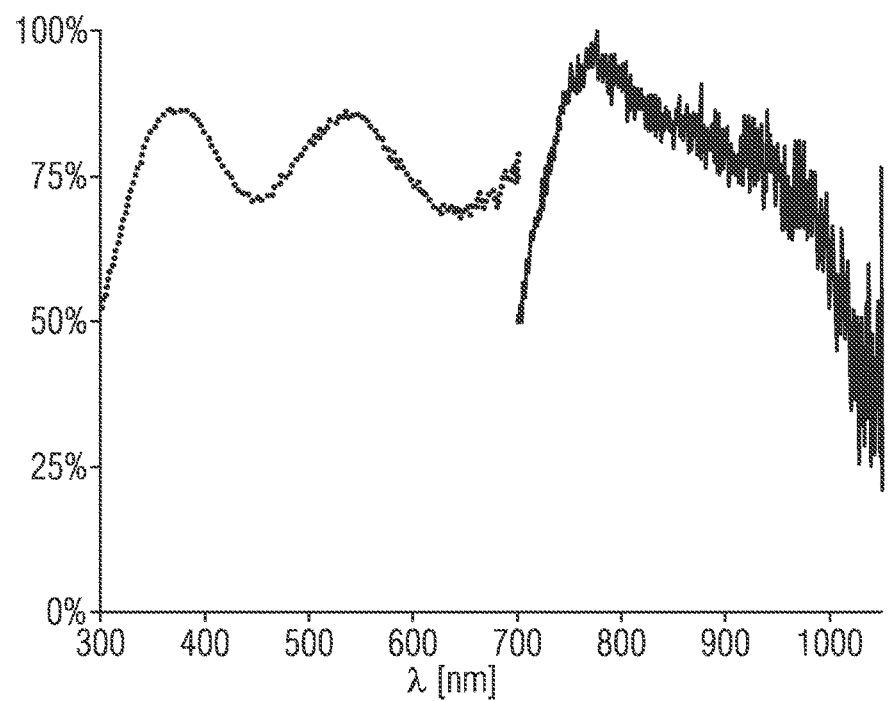
FIGS. 5 to 12 show the reflection coefficient and the emission of different embodiments of the conversion material.

Identical, similar elements or elements which act in an identical manner are provided with the same reference numerals in the figures. The figures and the size ratios of the elements with respect to each other, as illustrated in the figures, are not to be considered as being to scale. Rather, individual elements can be illustrated excessively large for improved clarity and/or for improved understanding.

DETAILED DESCRIPTION OF ILLUSTRATIVE EMBODIMENTS

The exemplified embodiment of a radiation-emitting optoelectronic device 1 as illustrated in FIG. 1 has a semiconductor chip 2, a rear side contact 15, a front side contact 16 and an active epitaxial layer sequence 9, wherein the active epitaxial layer sequence 9 emits red or blue primary radiation during operation. For example, the semiconductor chip is based upon aluminum indium gallium phosphide or indium gallium nitride.

The semiconductor chip 2 is attached to a first connection 4 by means of an electrically conductive connecting means with the rear side contact 15. The electrically conductive connecting means uses, e.g., a metallic solder or an adhesive. The front side contact 16 is connected to a second electrical connection 5 by means of a bond wire 17.

In the case of the exemplified embodiment illustrated in FIG. 1, the first and second electrical connections 4, 5 are embedded into an opaque, e.g., prefabricated main housing 10 having a recess 11. "Prefabricated" is to be understood to mean that the main housing 10 is already completely formed on the connections 4, 5, e.g., by injection molding, before the semiconductor chip 2 is mounted onto the connection 4. The main housing 10 comprises, e.g., an opaque synthetic material and the recess 11 is formed in terms of its shape as a reflector 18 for the primary radiation and secondary radiation, wherein the reflection can be achieved optionally by suitably coating the inner walls of the recess 11. Such main housings 10 are used in particular in surface-mountable light-emitting diodes. They are applied, prior to mounting of the semiconductor chip 2, onto a leadframe, which has the electrical connections 4, 5, e.g., by means of injection molding and/or transfer molding.

In the case of the exemplified embodiment of FIG. 1, the conversion element 6 is formed as a casting compound and fills the recess 11, as shown in FIG. 1. The conversion element comprises a conversion material and a matrix material, into which the conversion material is embedded. The matrix material is, e.g., a silicone. The conversion material is present in the form of converter particles and comprises or consists of $La_3Ga_{4.975}Cr_{0.025}GeO_{14}$ and $(Ga,Cr)_2O_3$. In this case, the conversion material has almost no defects in its crystal lattice so that, when the current is switched off, the conversion material does not exhibit any afterglow or does so only for a very short time period. The primary radiation emitted by the semiconductor chip 2 is converted at least partially by the conversion material into secondary radiation of a wavelength between 700 nm to 1050 nm.

A further exemplified embodiment of a radiation-emitting optoelectronic device described in this case is described in conjunction with FIG. 2. In the exemplified embodiment of FIG. 2, the conversion element 6 is formed as a layer. The conversion element 6 consists of a glass, in which converter particles, e.g., of a conversion material consisting of $La_3Ga_{4.95}Cr_{0.05}GeO_{14}$ and $(Ga,Cr)_2O_3$ are homogeneously distributed.

The conversion element 6 is applied directly onto the semiconductor chip 2. The semiconductor chip 2 and at least sub-regions of the electrical connection 4, 5 are surrounded by a radiation-permeable casing 13 which does not cause any change in wavelength or frequency of the radiation passing through the conversion element 6. The radiation-permeable casing can consist, e.g., of at least one of the following materials and/or can contain at least one of the following materials: silicone, epoxy, polyurethane or glass.

In the case of the exemplified embodiment illustrated in FIG. 3, the first and second electrical connections 4, 5 are embedded into an opaque, possibly prefabricated main housing 10 having a recess 11. As can be seen in FIG. 3, the free surfaces of the semiconductor chip 2 and sub-regions of the electrical connections 4 and 5 are surrounded at least partially and/or directly by a radiation-permeable casing 12. This radiation-permeable casing 12 does not cause any change in wavelength to the primary radiation emitted by the semiconductor chip 2. The radiation-permeable casing 12 consists, e.g., of one of the radiation-permeable materials already stated above or contains at least one of these materials. Furthermore, in this embodiment the recess 11 can be filled with a gas.

The recess 11 in FIG. 3 is covered by a conversion element 6 consisting of the ceramic conversion material, wherein the conversion element 6 is a plate 6 which is produced separately and is attached to the main housing 10. For example, it is a plate consisting of a $Ca_3Ga_{1.98}Cr_{0.02}Ge_4O_{14}$ ceramic.

In order to more effectively couple the light out of the conversion element 6 of FIG. 3, a lens-shaped cover 21 which reduces a total reflection of the radiation within the conversion element 6 can be provided on a lateral surface of the device at the radiation exit surface. This lens-shaped cover 21 can consist in particular of a radiation-permeable synthetic material or of a glass and can be, e.g., adhered onto the conversion element 6 or can be formed directly as a part of the conversion element 6.

In the case of the exemplified embodiment illustrated in FIG. 4, the first and second electrical connections 4, 5 are embedded into an opaque, possibly prefabricated main housing 10 having a recess 11. As can be seen in FIG. 4, the free surfaces of the semiconductor chip 2 and sub-regions of the electrical connections 4 and 5 are surrounded at least partially and/or directly by a radiation-permeable casing 12. This radiation-permeable casing 12 does not cause any change in wavelength to the primary radiation emitted by the semiconductor chip 2. The radiation-permeable casing 12 consists, e.g., of one of the radiation-permeable materials already stated above or contains at least one of these materials. Furthermore, in this embodiment the recess 11 can be filled with a gas. The conversion element 6 is arranged directly on the semiconductor chip 2. The conversion element 6 is formed as a plate and consists, e.g., of a $Na_{1.4}Ga_{4.95}Cr_{0.05}O_{8.2}$ ceramic.

In addition, an adhesive layer (not shown here) can be applied between the semiconductor chip 2 and the conversion element 6.

Preferably, the optoelectronic device 1 is an LED, wherein in FIGS. 1 to 4 the radiation is coupled out upwards via the conversion element 6.

FIGS. 5 to 12 show reflection coefficients (dotted line) and relative intensities of the emission (continuous line) of different exemplified embodiments of the conversion material. In each case, the wavelength λ in nm is plotted on the x-axis and the relative reflection coefficient or the relative intensity of the emission is plotted on the y-axis. In order to measure the emission spectra, the conversion material was introduced in the form of particles into a matrix material consisting of silicone and was arranged over a semiconductor chip with a primary radiation of 450 nm or 637 nm.

FIG. 5 shows the reflection coefficient (dotted line) and the relative intensity of the emission (continuous line) of the conversion material $La_3Ga_{4.975}Cr_{0.025}GeO_{14}$ with a secondary phase consisting of $(Ga,Cr)_2O_3$ at an excitation wavelength, i.e., a primary radiation of 450 nm. The conversion material demonstrates at about 450 nm and 640 nm the lowest reflection and therefore can be most effectively excited at about 450 nm and 620 nm, that is to say with a primary radiation in the blue and red spectral range. The conversion material has a broad and continuous emission between 700 and 1050 nm, wherein the relative intensity is in the range of 700 nm to about 1000 nm at over 50%. The maximum emission is at a wavelength of about 780 nm. The broad emission is based on the superimposition of two separate emission bands of $La_3Ga_{4.975}Cr_{0.025}GeO_{14}$ and $(Ga,Cr)_2O_3$ and the type of host lattice used.

The conversion material $La_3Ga_{4.975}Cr_{0.025}GeO_{14}$ with the secondary phase consisting of $(Ga,Cr)_2O_3$ was produced as follows: 36.27 mmol $La_2O_3$, 105.44 mmol $Ga_2O_3$, 42.18 mmol $GeO_2$, 2.11 mmol boric acid and 0.527 mmol $Cr_2O_3$ are processed in a mixer and a mortar mill to form a mixture. The mixer used is a speed mixer which is also defined as a dual asymmetrical centrifuge, that is to say a laboratory mixing system which is based upon the double rotation of a mixing beaker. The boric acid functions in this case as a fluxing agent which improves reactivity/crystal growth. The powder thus produced is transferred to a corundum pot and is annealed at 950° for four hours. After cooling to room temperature, the sintered powder is milled and sieved and is then subject to a second annealing step at 1300° for four hours. The sintered material obtained is pulverized with a mortar mill and is sieved with an analysis sieve having a mesh size of 30 μm in order to separate coarser particles (>30 μm).

Figure 6:
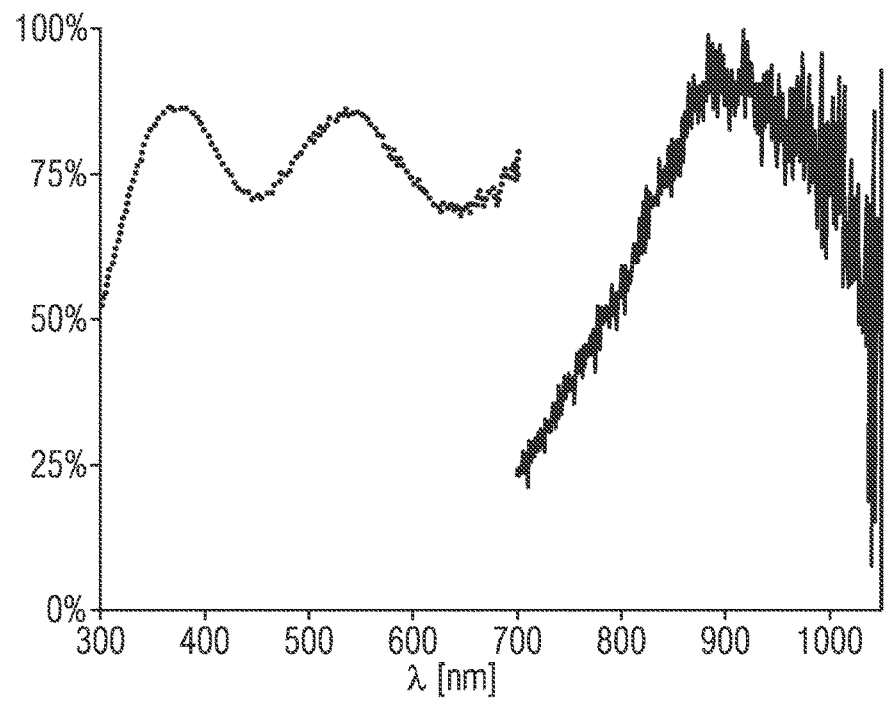

FIG. 6 shows the reflection coefficient (dotted line) and the relative intensity of the emission (continuous line) of the conversion material $La_3Ga_{4.975}Cr_{0.025}GeO_{14}$ with the secondary phase consisting of $(Ga,Cr)_2O_3$ at an excitation wavelength, i.e., a primary radiation of 637 nm. The reflection coefficient in dependence upon the wavelength corresponds to that illustrated in FIG. 5. The conversion material has a broad and continuous emission between 700 and 1050 nm, wherein the relative intensity is in the range of about 780 nm to about woo nm at over 50%. The maximum emission is at a wavelength of about 900 nm. The broad emission is based upon the superimposition of two separate emission bands of $La_3Ga_{4.975}Cr_{0.025}GeO_{14}$ and $(Ga,Cr)_2O_3$.

Figure 7:
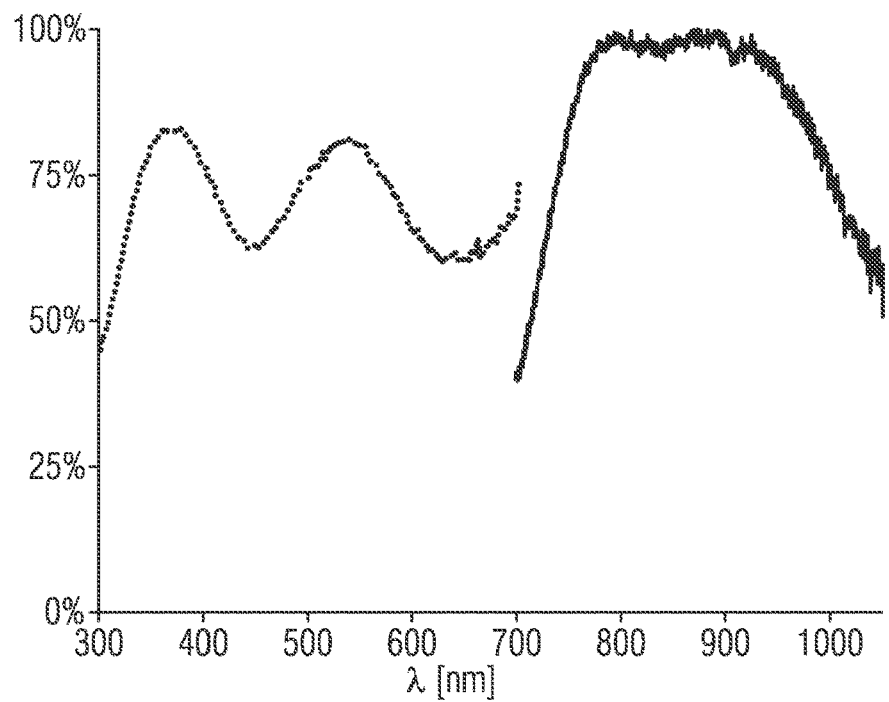

FIG. 7 shows the reflection coefficient (dotted line) and the relative intensity of the emission (continuous line) of the conversion material $La_3Ga_{4.95}Cr_{0.05}GeO_{14}$ with the secondary phase consisting of $(Ga,Cr)_2O_3$ at an excitation wavelength, i.e., a primary radiation of 450 nm. The conversion material demonstrates at about 450 nm and 640 nm the lowest reflection and therefore can be most effectively excited at about 450 nm and 620 nm, that is to say with a primary radiation in the blue and red spectral range. The conversion material has a broad and continuous emission between 700 and 1050 nm, wherein the relative intensity is in the range of 700 nm to about 1050 nm at over 50%. The maximum emission is at a wavelength of about 780 nm to 920 nm. The broad emission is based on the superimposition of two separate emission bands of $La_3Ga_{4.975}Cr_{0.025}GeO_{14}$ and $(Ga,Cr)_2O_3$ and the type of host lattice used.

The conversion material $La_3Ga_{4.95}Cr_{0.05}GeO_{14}$ with the secondary phase consisting of $(Ga,Cr)_2O_3$ was produced as follows: 63.15 mmol $La_2O_3$, 105.26 mmol $Ga_2O_3$, 42.10 mmol $GeO_2$, 2.11 mmol boric acid and 1.052 mmol $Cr_2O_3$ are processed in a mixer and a mortar mill to form a mixture. The mixer used is a speed mixer. The powder thus produced is transferred to a corundum pot and is annealed at 950° for four hours. After cooling to room temperature, the sintered powder is milled and sieved and is then subject to a second annealing step at 1300° for four hours. The sintered material obtained was pulverized with a mortar mill and sieved with an analysis sieve having a mesh size of 30 μm in order to separate coarser particles (>30 μm).

Figure 8:
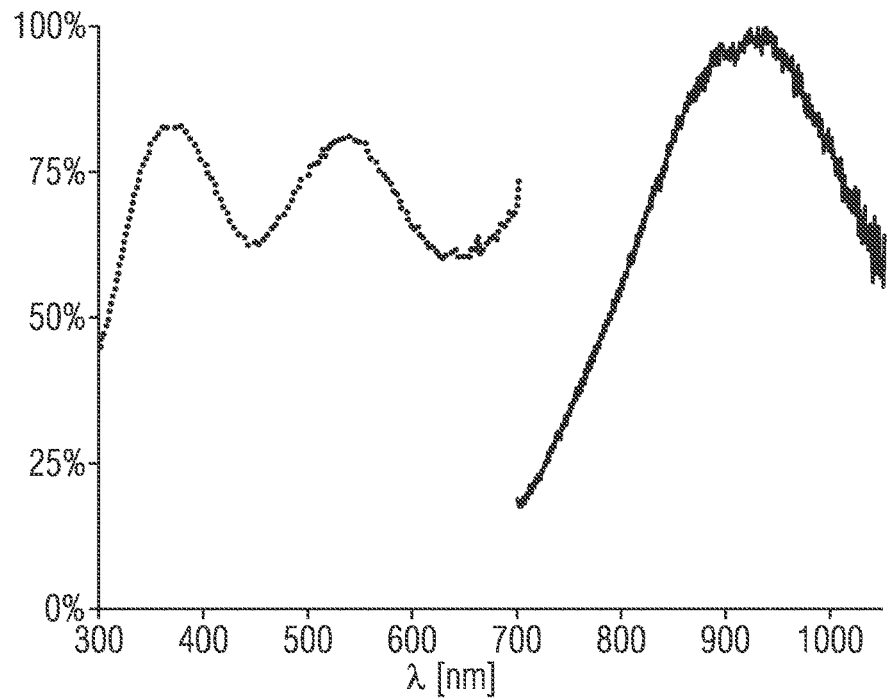

FIG. 8 shows the reflection coefficient (dotted line) and the relative intensity of the emission (continuous line) of the conversion material $La_3Ga_{4.95}Cr_{0.05}GeO_{14}$ with a secondary phase consisting of $(Ga,Cr)_2O_3$ at an excitation wavelength, i.e., a primary radiation of 637 nm. The reflection coefficient in dependence upon the wavelength corresponds to that illustrated in FIG. 7. The conversion material has a broad and continuous emission between 700 and 1050 nm, wherein the relative intensity is in the range of about 800 nm to about 1050 nm at over 50%. The maximum emission is at a wavelength of about 910 nm. The broad emission is based on the superimposition of two separate emission bands of $La_3Ga_{4.975}Cr_{0.025}GeO_{14}$ and $(Ga,Cr)_2O_3$ and the type of host lattice used.

Figure 9:
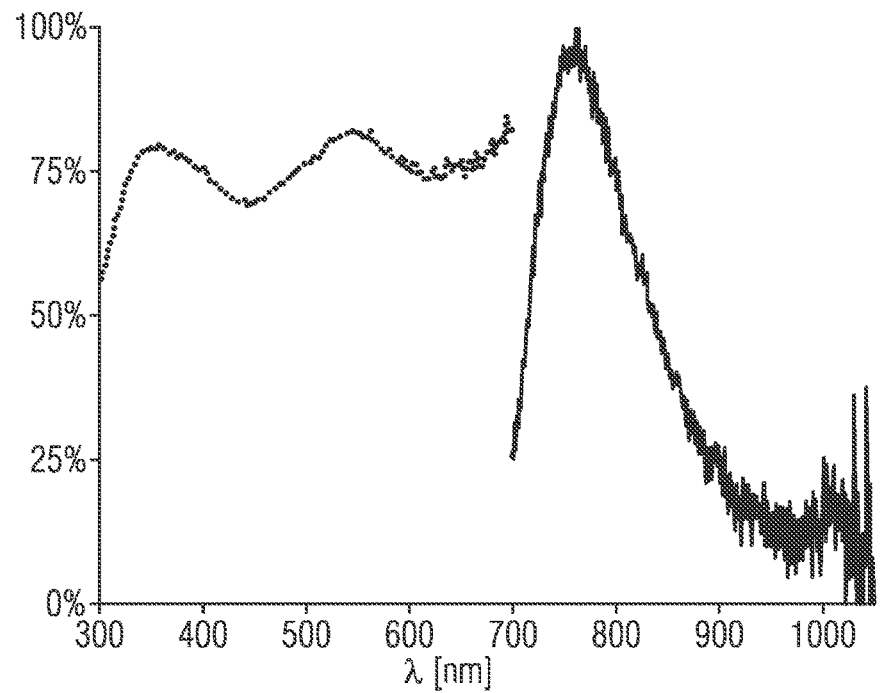

FIG. 9 shows the reflection coefficient (dotted line) and the relative intensity of the emission (continuous line) of the conversion material $Ca_3Ga_{1.98}Cr_{0.02}Ge_4O_{14}$ at an excitation wavelength, i.e., a primary radiation of 450 nm. The conversion material demonstrates at about 450 nm and 620 nm the lowest reflection and therefore can be most effectively excited at these wavelengths, that is to say with a primary radiation in the blue and red spectral range. The conversion material has a broad and continuous emission between 700 and 900 nm, wherein the relative intensity is in the range of 700 nm to about 850 nm at over 50%. The maximum emission is at a wavelength of about 760 nm.

The conversion material $Ca_3Ga_{1.98}Cr_{0.02}Ge_4O_{14}$ was produced as follows: 49.49 mmol $CaCO_3$, 0.33 mmol $CaF_2$, 16.50 mmol $Ga_2O_3$, 65.99 mmol $GeO_2$, and 0.165 mmol $Cr_2O_3$ are processed in a mixer and a mortar mill to form a mixture. The mixer used is a speed mixer. The powder thus produced is transferred to a corundum pot and is annealed at 1150° for four hours. After cooling to room temperature, the sintered powder is milled and sieved and is then subject to a second annealing step at 1200° for four hours. The sintered material obtained was pulverized with a mortar mill and sieved with an analysis sieve having a mesh size of 30 μm in order to separate coarser particles (>30 μm).

Figure 10:
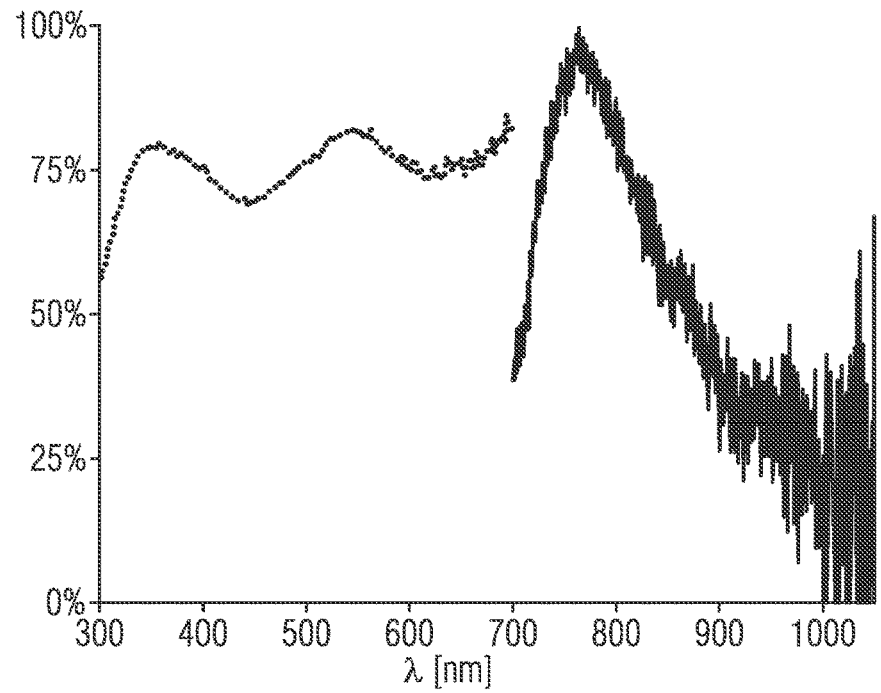

FIG. 10 shows the reflection coefficient (dotted line) and the relative intensity of the emission (continuous line) of the conversion material $Ca_3Ga_{1.98}Cr_{0.02}Ge_4O_{14}$ at an excitation wavelength, i.e., a primary radiation of 637 nm. The reflection coefficient in dependence upon the wavelength corresponds to that illustrated in FIG. 9. The conversion material has a broad and continuous emission between 700 and 900 nm, wherein the relative intensity is in the range of about 700 nm to about 860 nm at over 50%. The maximum emission is at a wavelength of about 760 nm.

Figure 11:
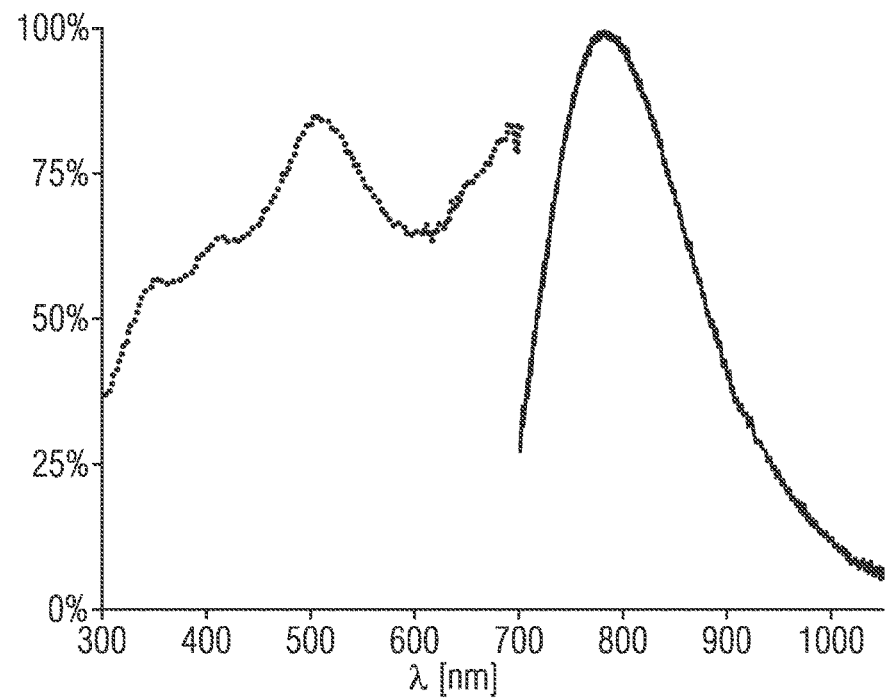

FIG. 11 shows the reflection coefficient (dotted line) and the relative intensity of the emission (continuous line) of the conversion material $Na_{1.4}Ga_{4.95}Cr_{0.05}O_{8.2}$ at an excitation wavelength, i.e., a primary radiation of 450 nm. The conversion material demonstrates at about 440 nm and 610 nm low reflections and therefore can be most effectively excited at these wavelengths, that is to say with a primary radiation in the blue and red spectral range. The conversion material has a broad and continuous emission between 700 and 900 nm, wherein the relative intensity is in the range of 700 nm to about 890 nm at over 50%. The maximum emission is at a wavelength of about 790 nm.

The conversion material $Na_{1.4}Ga_{4.95}Cr_{0.05}O_{8.2}$ was produced as follows: 64.03 mmol $Na_2CO_3$, 228.69 mmol $Ga_2O_3$ and 2.29 mmol $Cr_2O_3$ are processed in a mixer and a mortar mill to form a mixture. The mixer used is a speed mixer. The powder thus produced is transferred to a corundum pot and is annealed at 1250° for four hours. After cooling to room temperature, the sintered powder is milled and sieved and is then subject to a second annealing step at 1250° for four hours. The sintered material obtained was pulverized with a mortar mill and sieved with an analysis sieve having a mesh size of 30 μm in order to separate coarser particles (>30 μm).

Figure 12:
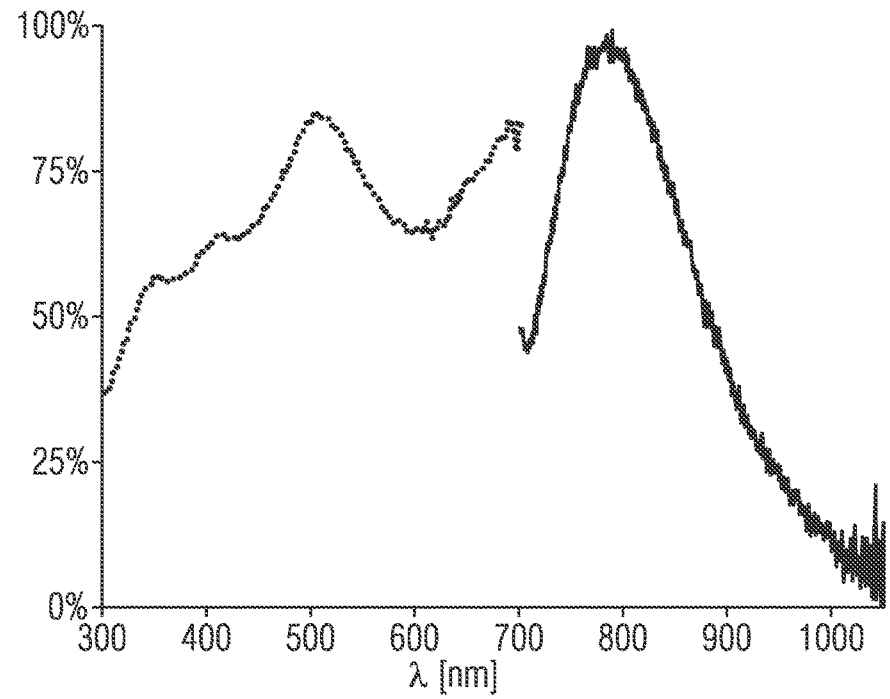

FIG. 12 shows the reflection coefficient (dotted line) and the relative intensity of the emission (continuous line) of the conversion material $Na_{1.4}Ga_{4.95}Cr_{0.05}O_{8.2}$ at an excitation wavelength, i.e., a primary radiation of 665 nm. The reflection coefficient in dependence upon the wavelength corresponds to that illustrated in FIG. 11. The conversion material has a broad and continuous emission between 700 and 900 nm, wherein the relative intensity is in the range of 700 nm to about 890 nm at over 50%. The maximum emission is at a wavelength of about 790 nm.

Figure 13:
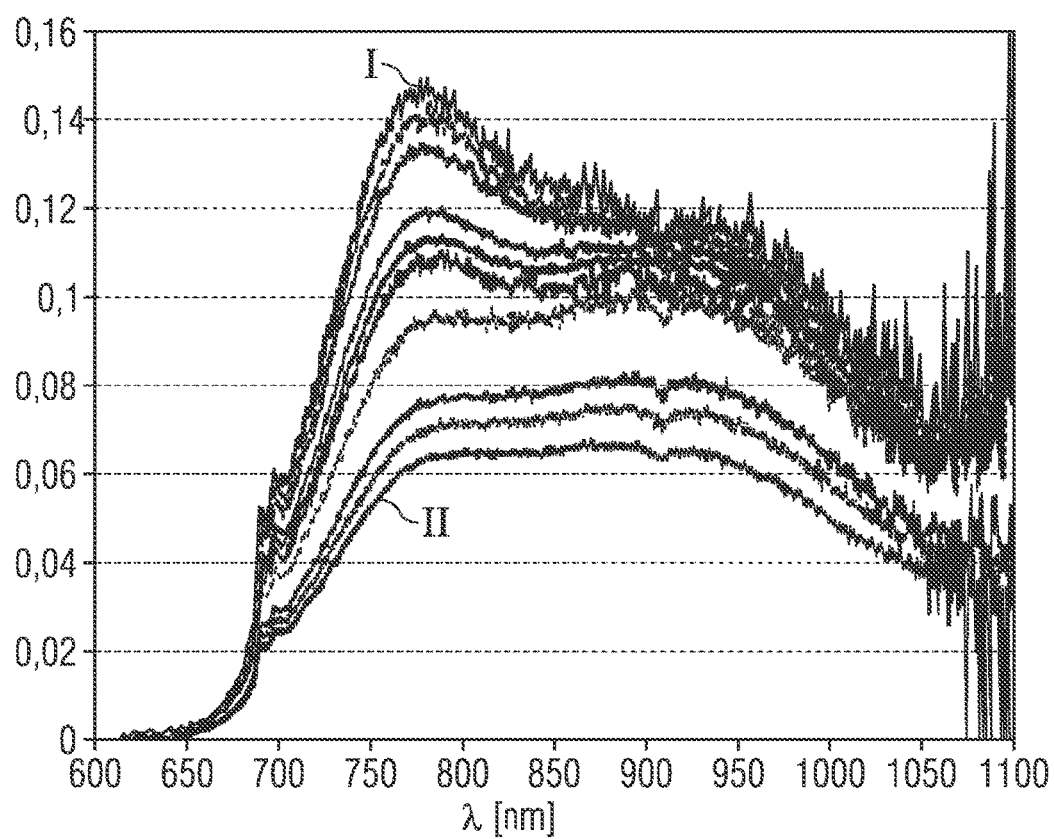
FIG. 13 shows the emission power of a conversion material in dependence upon the current intensity, at which the semiconductor chip which generates the primary radiation is operated.

In FIG. 13, the wavelength λ in nm is plotted on the x-axis and the relative intensity of the emission for the luminescent material $La_3Ga_{4.95}Cr_{0.05}GeO_{14}$, which contains $(Ga,Cr)_2O_3$ as a secondary phase, is plotted on the y-axis. The relative intensity of the emission was recorded at different current intensities, wherein the curve designated by the reference sign I indicates the relative intensity of a current intensity of 5 mA and the curve designated by the reference sign II indicates the relative intensity at a current intensity of moo mA. It is apparent that the intensity of the emission in the region of 780 nm with an increasing current intensity decreases more than the intensity of the emission in the region of 950 nm. From this it is apparent that there are two separate emission bands, one results from $La_3Ga_{4.95}Cr_{0.05}GeO_{14}$ and the other results from $(Ga,Cr)_2O_3$. These emission bands have different quantum efficiencies depending upon the intensity of the primary radiation. In order to counteract this decrease in emission intensity as current intensities increase, a second or further conversion material can be added, such as, e.g., $Na_{1.4}Ga_{4.95}Cr_{0.05}O_{8.2}$ which has only one emission band and its maximum is specifically at 780 nm, as can be seen in FIGS. 11 and 12. Therefore, such a combination of conversion materials serves to achieve a stable and broad emission.

FIGS. 14 to 17 show the relative intensities of the emission of different exemplified embodiments of the conversion material in accordance with the invention in comparison with a conventional semiconductor chip which emits primary radiation in the infrared range. In each case, the wavelength λ in nm is plotted on the x-axis and the relative intensity of the emission is plotted on the y-axis. In order to measure the emission spectra, the conversion material was introduced in the form of particles into a matrix material consisting of silicone and was arranged over a semiconductor chip with a primary radiation in the blue and red spectral range.

Figure 14:
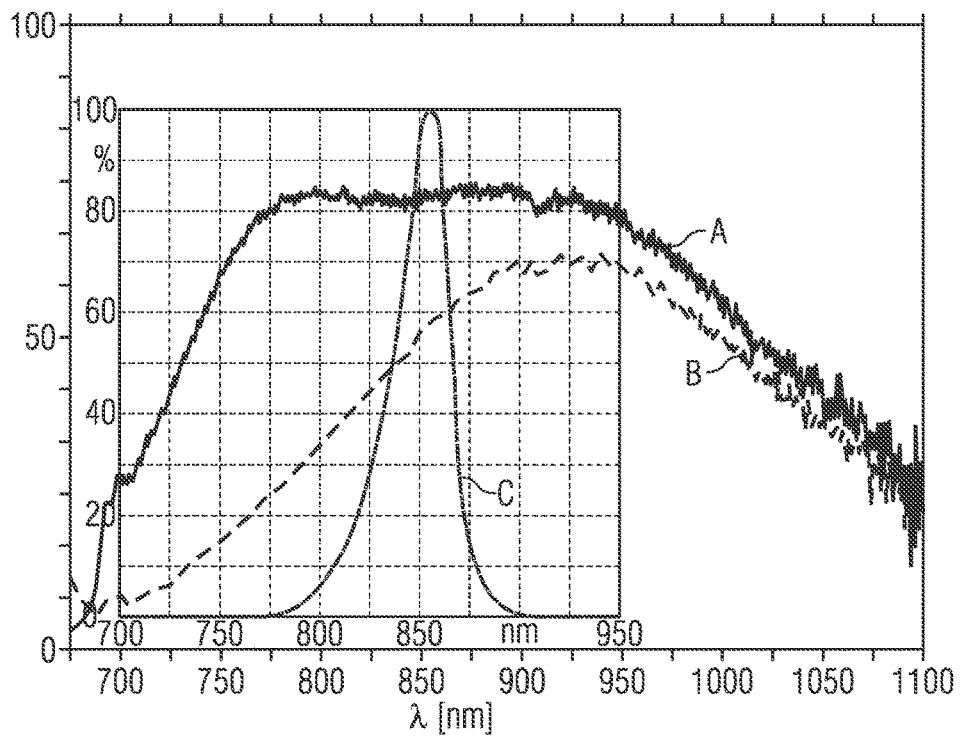
FIGS. 14 to 17 show the emission of different exemplified embodiments of the conversion material in accordance with the invention in comparison with a conventional semiconductor chip which emits primary radiation in the infrared range.

FIG. 14 shows the relative intensity of the emission of the conversion material $La_3Ga_{4.95}Cr_{0.05}GeO_{14}$ which as a secondary phase contains $(Ga,Cr)_2O_3$ in the case of an excitation with a primary radiation in the blue spectral range (curve designated by the reference sign A) and in the case of an excitation with a primary radiation in the red spectral range (curve designated by the reference sign B). The curve designated by the reference sign C shows the relative intensity of the emission of a conventional semiconductor chip which emits primary radiation in the infrared range. As can be seen in curve A, the intensity of the secondary radiation, i.e., the emission, is in a range of about 700 nm to about 1050 nm at over 20% of the maximum intensity of the secondary radiation. In this case, the maximum intensity is about 80%. As can be seen in curve B, the intensity of the secondary radiation, i.e., the emission, is in a range of about 750 nm to about 1050 nm over 20% of the maximum intensity of the secondary radiation. In this case, the maximum intensity is about 70%. The intensity of the secondary radiation varies in curve A in a range of about 775 nm to 950 nm by at the most 5 percent per nm, it is almost constant in one region and varies in curve B in a range of about 875 nm to 975 nm by at the most 5 percent per nm. The deflections in curves A and B are noise, i.e., not measurement points, but instead are measurement artifacts which can be eliminated by a longer measurement time. It is apparent that, in comparison with the conversion material in accordance with the invention, the conventional semiconductor chip is not suitable for use in spectrometers or sensor applications because the requirements of a broad and continuous emission in the range of 700 nm to 1050 nm are not met. As can be seen in curve C, the intensity of the emission is only in a range of about 825 nm to 875 nm, i.e., a range of about 50 nm over 20% of the maximum intensity of the emission which in this case is 100%. Therefore, this is a narrow-band emission.

Figure 15A:
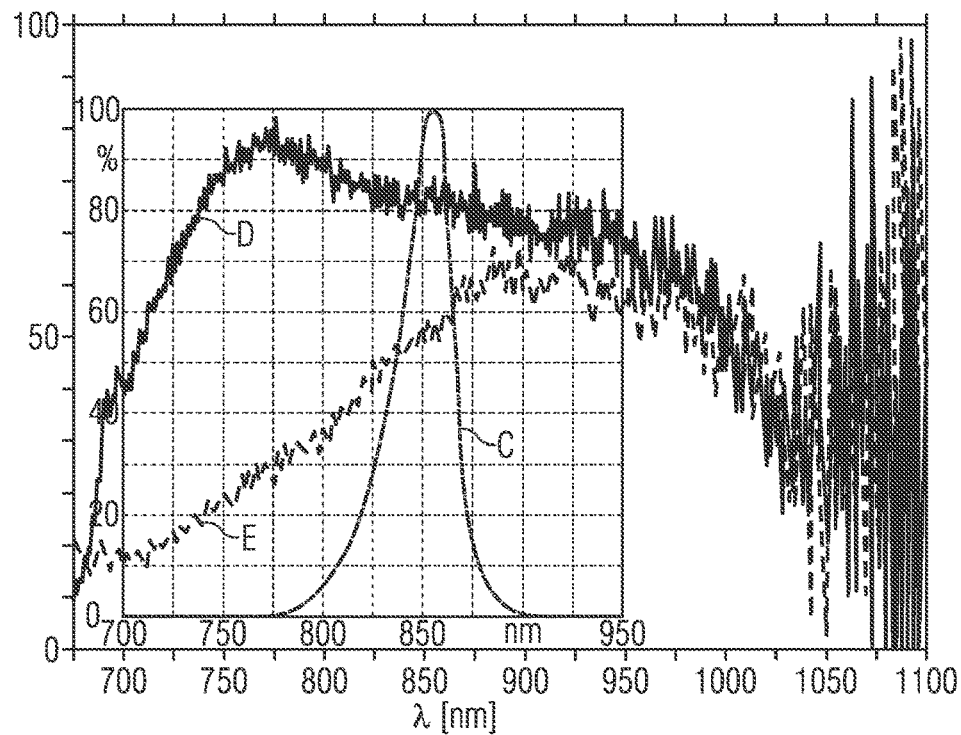

FIG. 15A shows the relative intensity of the emission of the conversion material $La_3Ga_{4.975}Cr_{0.025}GeO_{14}$ which as a secondary phase contains $(Ga,Cr)_2O_3$ in the case of an excitation with a primary radiation in the blue spectral range (curve designated by the reference sign D) and in the case of an excitation with a primary radiation in the red spectral range (curve designated by the reference sign E). The emission spectra are a superimposition of the emission of $La_3Ga_{4.975}Cr_{0.025}GeO_{14}$ and $(Ga,Cr)_2O_3$. The curve designated by the reference sign C shows the relative intensity of the emission of the conventional semiconductor chip which emits primary radiation in the infrared range. As can be seen in curve D, the intensity of the secondary radiation, i.e., the emission, is in a range of about 700 nm to about 1000 nm over 20% of the maximum intensity of the secondary radiation. In this case, the maximum intensity is about 90%. As can be seen in curve E, the intensity of the secondary radiation, i.e., the emission, is in a range of about 750 nm to about 1050 nm over 20% of the maximum intensity of the secondary radiation. In this case, the maximum intensity is about 70%. Moreover, the intensity of the secondary radiation of the curves D and E varies in a region of at least 40 nm by not more than 5 percent per nm. The deflections in curves D and E are noise, i.e., not measurement points, but instead are measurement artifacts which can be eliminated by a longer measurement time. It is apparent that, in comparison with the conversion material in accordance with the invention, the conventional semiconductor chip is not suitable for use in spectrometers or sensor applications because the requirements of a broad and continuous emission in the range of 700 nm to 1050 nm are not met. As can be seen in curve C, the intensity of the emission is only in one range of about 825 nm to 875 nm, i.e., a range of about 50 nm over 20% of the maximum intensity of the emission which in this case is 100%.

Figure 15B:
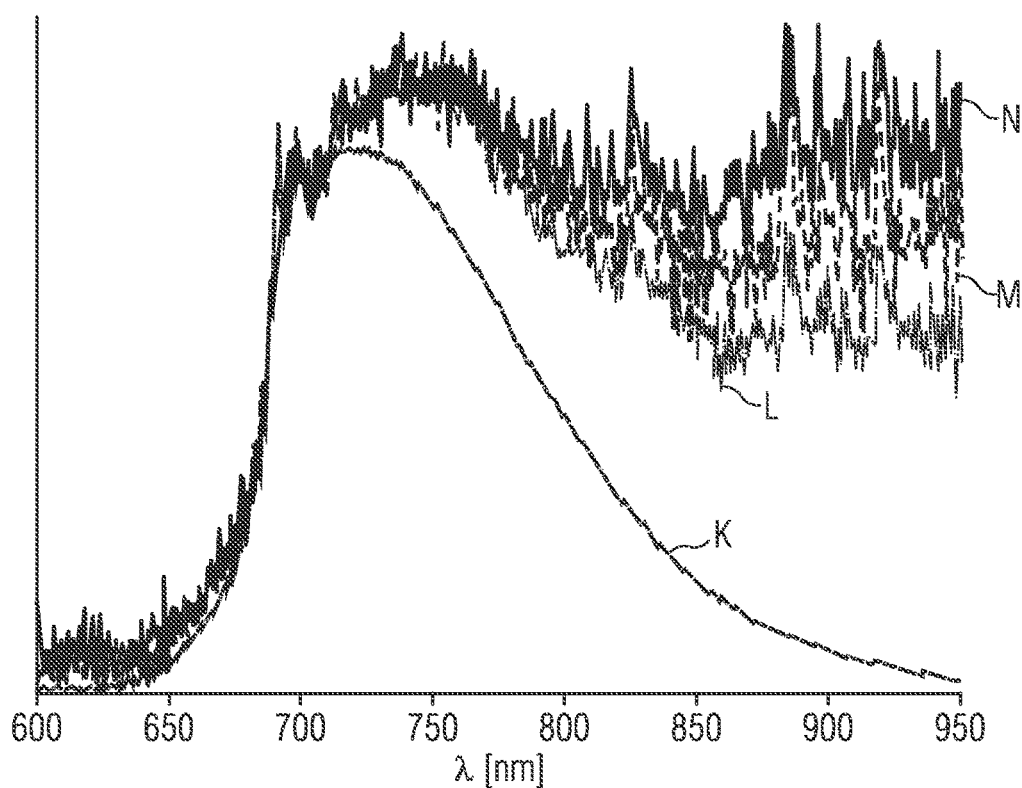

FIG. 15B shows the relative intensity of the emission of the conversion material $(Ga,Cr)_2O_3$ (reference sign K) and $La_3(Ga,Cr)_5GeO_{14}$ which as a secondary phase contains $(Ga,Cr)_2O_3$ (reference signs L, M, N) in the case of an excitation with a primary radiation in the blue spectral range. The table of FIG. 15B shows the respective composition of the conversion material. The first column indicates in each case the reference sign and the second and third columns indicate in each case the proportion of $La_3(Ga,Cr)_5GeO_{14}$ and $\beta\text{-}(Ga,Cr)_2O_3$ in weight percent. The proportion of the secondary phase $\beta\text{-}(Ga,Cr)_2O_3$ was determined radiographically. As can be seen, the ratio varies in the region of about 750 nm and in the region of about 920 nm depending upon the present proportion of $\beta\text{-}(Ga,Cr)_2O_3$. As the weight proportion of $\beta\text{-}(Ga,Cr)_2O_3$ increases, the relative intensity of the emission decreases in the region of 920 nm and increases in the region of 750 nm.

Figure 16:
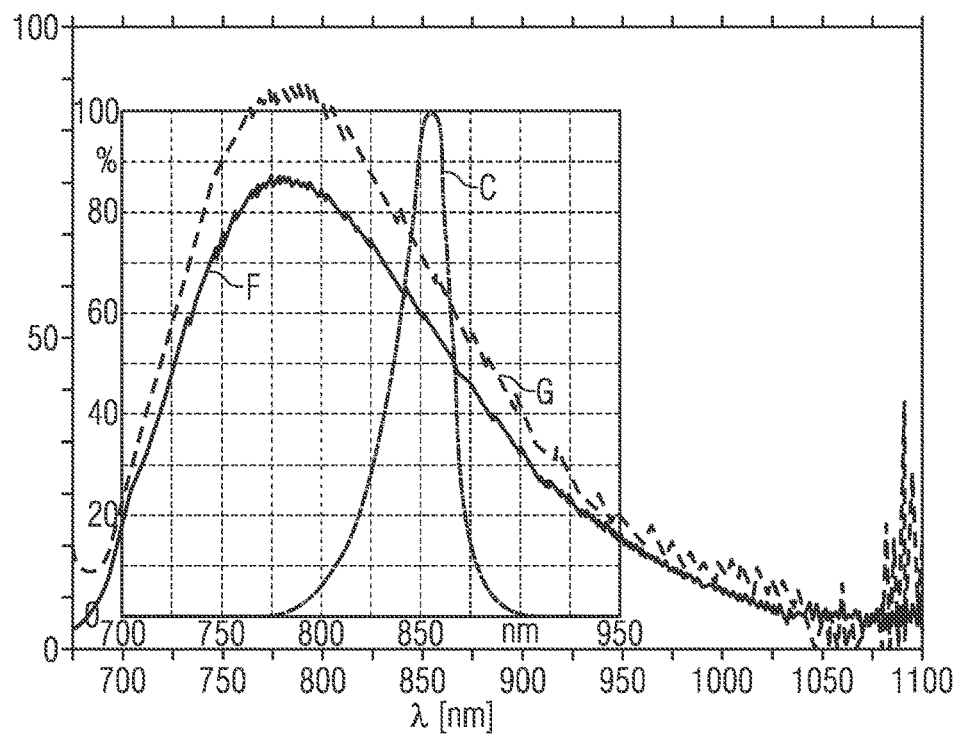

FIG. 16 shows the relative intensity of the emission of the conversion material $Na_{1.4}Ga_{4.95}Cr_{0.05}O_{8.2}$ in the case of an excitation with a primary radiation in the blue spectral range (curve designated by the reference sign F) and in the case of an excitation with a primary radiation in the red spectral range (curve designated by the reference sign G). The curve designated by the reference sign C shows the relative intensity of the emission of a conventional semiconductor chip which emits primary radiation in the infrared range. As can be seen in curve G, the intensity of the secondary radiation, i.e., the emission, is in a range of about 700 nm to about 925 nm over 20% of the maximum intensity of the secondary radiation. In this case, the maximum intensity is about 100%. As can be seen in curve F, the intensity of the secondary radiation, i.e., the emission, is in a range of about 700 nm to about 925 nm over 20% of the maximum intensity of the secondary radiation. Moreover, the intensity of the secondary radiation of the curves G and F varies in a region of at least 40 nm by not more than 5 percent per nm. The deflections in curves G and F are noise, i.e., not measurement points, but instead are measurement artifacts which can be eliminated by a longer measurement time. It is apparent that, in comparison with the conversion material in accordance with the invention, the conventional semiconductor chip is not suitable for use in spectrometers or sensor applications because the requirements of a broad and continuous emission in the range of 700 nm to 1050 nm are not met. As can be seen in curve C, the intensity of the emission is only in range of about 825 nm to 875 nm, i.e., a range of about 50 nm over 20% of the maximum intensity of the emission which in this case is 100%.

Figure 17:
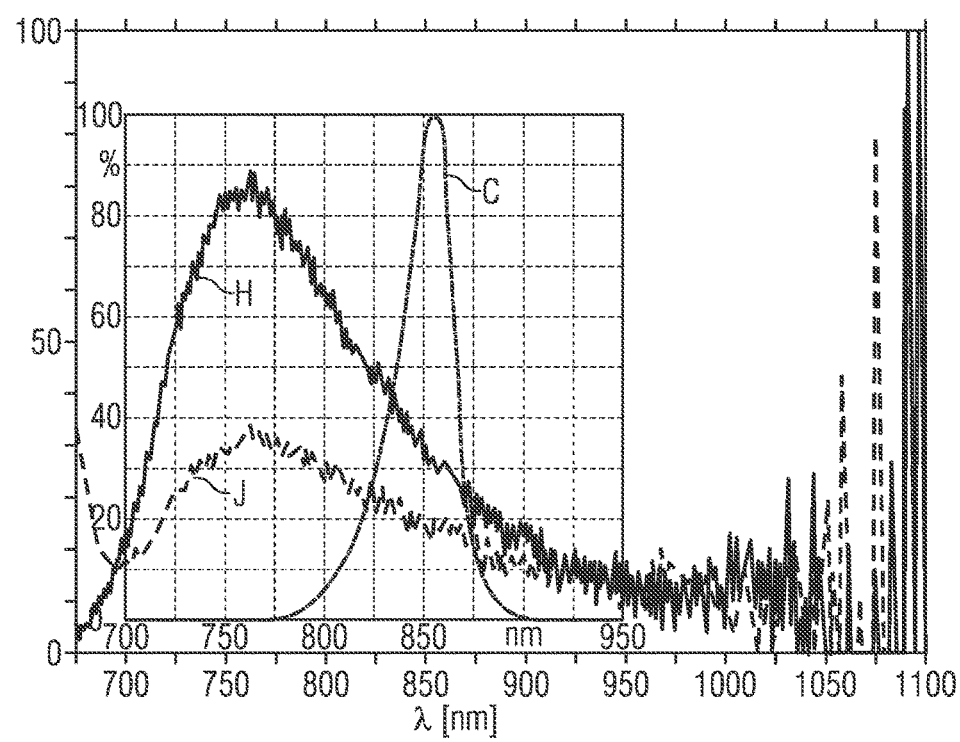

FIG. 17 shows the relative intensity of the emission of the conversion material $Ca_3Ga_{1.98}Cr_{0.002}Ge_4O_{14}$ in the case of an excitation with a primary radiation in the blue spectral range (curve designated by the reference sign H) and in the case of an excitation with a primary radiation in the red spectral range (curve designated by the reference sign J). The curve designated by the reference sign C shows the relative intensity of the emission of the conventional semiconductor chip which emits primary radiation in the infrared range. As can be seen in curve H, the intensity of the secondary radiation, i.e., the emission, is in a range of about 700 nm to about 850 nm over 20% of the maximum intensity of the secondary radiation. As can be seen in curve J, the intensity of the secondary radiation, i.e., the emission, is in a range of about 725 nm to about 950 nm over 20% of the maximum intensity of the secondary radiation. In this case, the maximum intensity is about 35%. Moreover, the intensity of the secondary radiation of the curves H and J varies in a region of at least 40 nm by not more than 5 percent per nm. The deflections in curves H and J are noise, i.e., not measurement points, but instead are measurement artifacts which can be eliminated by a longer measurement time. It is apparent that, in comparison with the conversion material in accordance with the invention, the conventional semiconductor chip is not suitable for use in spectrometers or sensor applications because the requirements of a broad and continuous emission in the range of 700 nm to 1050 nm are not met.

Figure 18:
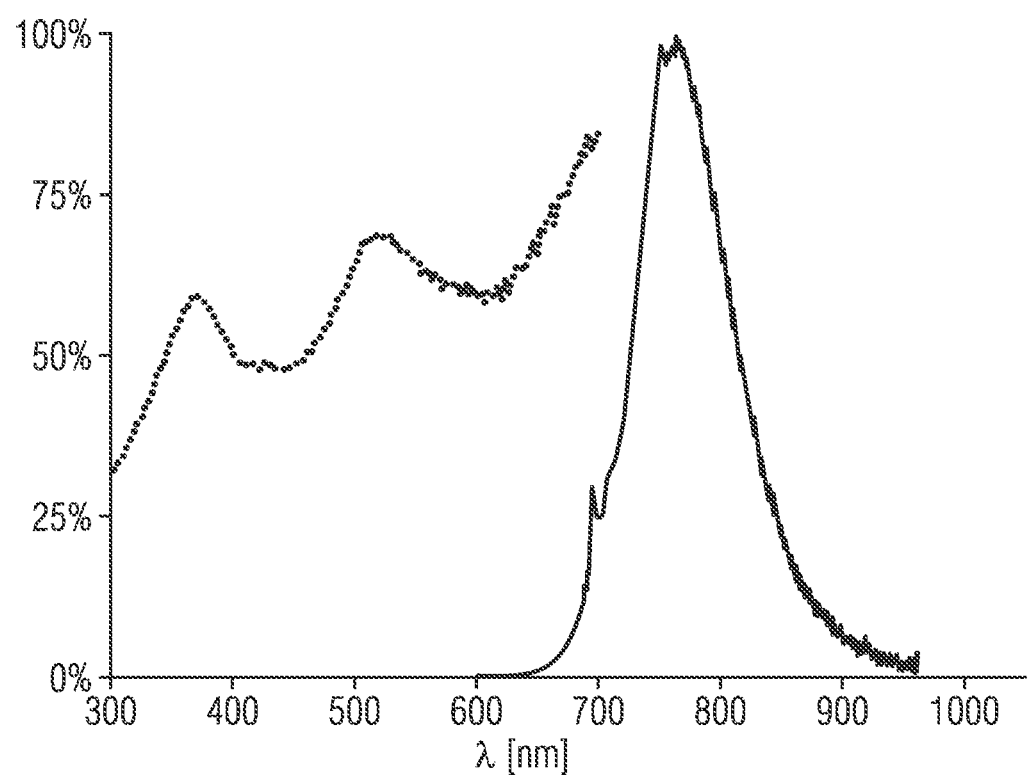
FIG. 18 shows the reflection coefficient and the emission of one embodiment of the conversion material.

FIG. 18 shows the reflection coefficient (dotted line) and the relative intensity of the emission (continuous line) of $SrGa_{11.88}Cr_{0.12}O_{19}$ as the conversion material at an excitation wavelength, i.e., a primary radiation of 460 nm. In each case, the wavelength λ in nm is plotted on the x-axis and the relative reflection coefficient or the relative intensity of the emission is plotted on the y-axis. In order to measure the emission spectra, the conversion material was introduced in the form of particles into a matrix material consisting of silicone excited with a primary radiation of 460 nm. The conversion material demonstrates at about 460 nm and 600 nm the lowest reflection and therefore can be most effectively excited at these wavelengths, that is to say with a primary radiation in the blue and red spectral range. The conversion material has a broad and continuous emission between 720 and 780 nm, wherein the relative intensity is in the range of 700 nm to about 800 nm at over 50%. The maximum emission is at a wavelength of about 770 nm.

The conversion material $SrGa_{11.88}Cr_{0.12}O_{19}$ was produced as follows: 14.96 mmol $SrCO_3$, 0.78 mmol $SrF_2$, 93.53 mmol $Ga_2O_3$ and 0.94 mmol $Cr_2O_3$ are processed in a mixer to form a mixture. The mixer used is a speed mixer. The powder thus produced is transferred to a corundum pot and is annealed at 1450° for four hours. After cooling to room temperature, the sintered material obtained was pulverized with a mortar mill and sieved with an analysis sieve having a mesh size of 30 μm in order to separate coarser particles (>30 μm).

Figure 19:
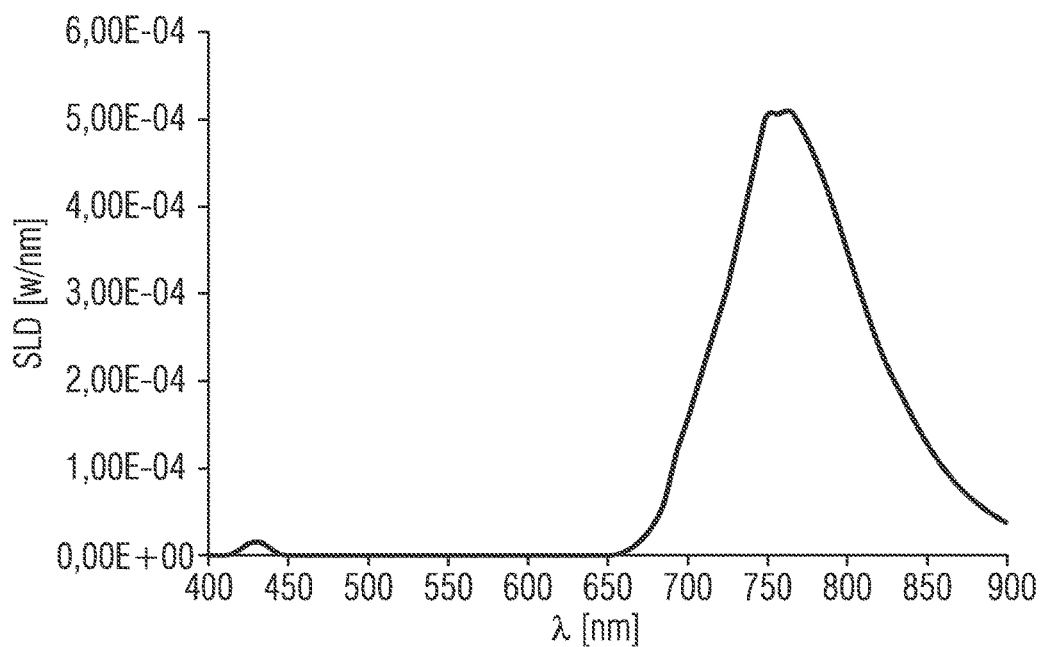
FIGS. 19 and 20 show emission spectra of radiation-emitting devices in accordance with the invention.

FIG. 19 shows an emission spectrum of a radiation-emitting device. The wavelength λ in nm is indicated on the x-axis and the spectral power density SLD in W/nm at 700 mA operating current is indicated on the y-axis. A blue-emitting InGaN semiconductor chip having a dominant wavelength of 440 to 445 nm was adhered and electrically connected on a substrate. The semiconductor chip was cast with a mixture consisting of $SrGa_{11.88}Cr_{0.12}O_{19}$ as the conversion material and silicone. The proportion of conversion material is 30 weight percent in relation to the total quantity of conversion material and silicone. At an operating current of 700 mA, 40 mW near-infrared radiation was emitted in a range of 760 nm+/−50 nm. In the range of 760 nm+/−20 nm the light current was 20 mW.

Figure 20:
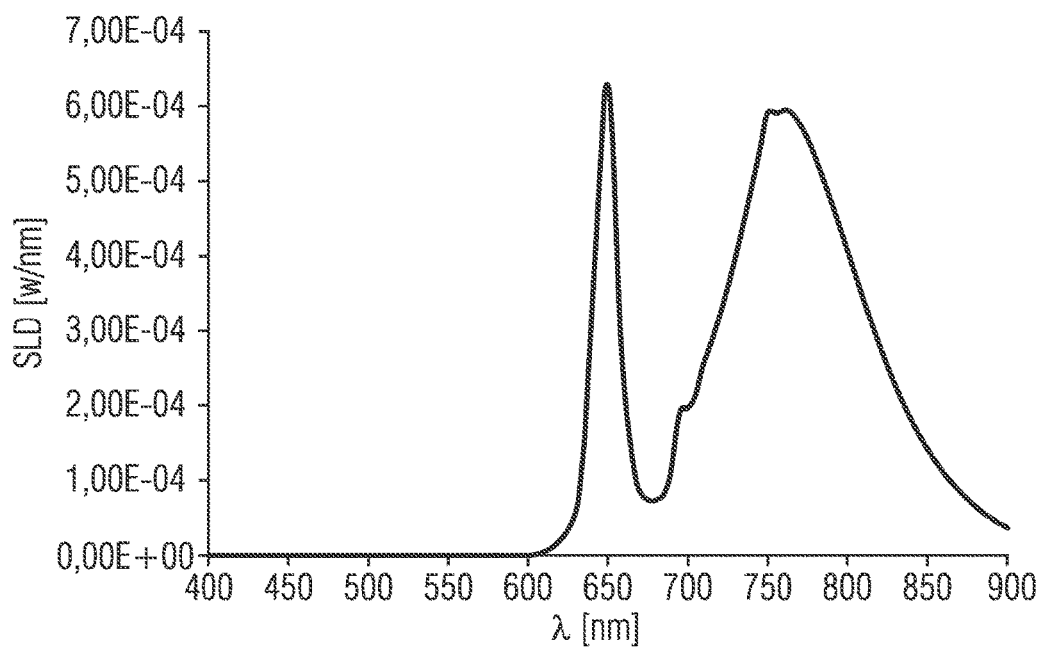

FIG. 20 shows an emission spectrum of a radiation-emitting device. The wavelength λ in nm is indicated on the x-axis and the spectral power density SLD in W/nm at 700 mA operating current is indicated on the y-axis. A red-emitting AlGaInP semiconductor chip having a dominant wavelength of 635 nm was adhered and electrically connected on a substrate. The semiconductor chip was cast with a mixture consisting of $SrGa_{11.88}Cr_{0.12}O_{19}$ as the conversion material and silicone. The proportion of conversion material is 30 weight percent in relation to the total quantity of conversion material and silicone. At an operating current of 700 mA, 47 mW near-infrared radiation was emitted in a range of 760 nm+/−50 nm. In the range of 760 nm+/−20 nm the light current was 24 mW.

The description made with reference to the exemplified embodiments does not restrict the invention to these embodiments. Rather, the invention encompasses any new feature and any combination of features, including in particular any combination of features in the claims, even if this feature or this combination is not itself explicitly indicated in the claims or exemplified embodiments.

The invention claimed is:

1. A radiation-emitting optoelectronic device, the device comprising:
    a semiconductor chip configured to emit a primary radiation during operation of the device; and
    a conversion element configured to convert the primary radiation emitted by the semiconductor chip into a secondary radiation of a wavelength between 700 nm and 2000 nm, the conversion element comprising a conversion material which comprises Cr and/or Ni ions and a host material, wherein the host material comprises $Ln_3Ga_5GeO_{14}$ and $Ga_2O_3$, and wherein Ln=La, Ce, Pr, Nd, Pm, Sm, Eu, Gd, Tb, Dy, Ho, Er, Tm, Yb and/or Lu.

2. The radiation-emitting optoelectronic device according to claim 1, wherein the conversion material comprises $Cr^{3+}$ and/or $Ni^{2+}$ ions.

3. The radiation-emitting optoelectronic device according to claim 1, wherein the Cr and/or Ni ions partially replace metals of the host material.

4. The radiation-emitting optoelectronic device according to claim 3, wherein the Cr and/or Ni ions replace 0.01 to 10 mol % of a metal of the host material.

5. A method for using the radiation-emitting optoelectronic device according to claim 1, the method comprising:
    placing the device in a spectrometer.

6. A method for using the radiation-emitting optoelectronic device according to claim 1, the method comprising:
    placing the device in an endoscope.

7. The radiation-emitting optoelectronic device according to claim 1, wherein during operation of the device, the conversion material converts the primary radiation emitted by the semiconductor chip into a secondary radiation of a wavelength between 700 nm and 1100 nm.

8. The radiation-emitting optoelectronic device according to claim 1, wherein the conversion element is part of a casting compound of the semiconductor chip or the conversion element forms the casting compound.

9. The radiation-emitting optoelectronic device according to claim 8, wherein the conversion element is a layer and is disposed directly onto the semiconductor chip.

10. The radiation-emitting optoelectronic device according to claim 1, wherein the conversion element is a plate or film which is disposed over the semiconductor chip.

11. The radiation-emitting optoelectronic device according to claim 1, wherein the conversion element comprises a silicone as a matrix material.

12. The radiation-emitting optoelectronic device according to claim 1, wherein the conversion material comprises Ln3(Ga1−xNix)5GeO(28−5x)/2 and (Ga1−xNix)2O3−x, and wherein x=0.0001-0.1 and Ln=La, Ce, Pr, Nd, Pm, Sm, Eu, Gd, Tb, Dy, Ho, Er, Tm, Yb and/or Lu.

13. The radiation-emitting optoelectronic device according to claim 1, wherein the conversion material comprises $Ln_3(Ga_{1-x'}Cr_{x'})_5GeO_{14}$ and $(Ga_{1-x'}Cr_{x'})_2O_3$, and wherein x'=0.0001-0.1 and Ln=La, Ce, Pr, Nd, Pm, Sm, Eu, Gd, Tb, Dy, Ho, Er, Tm, Yb and/or Lu.

14. A method for producing a radiation-emitting optoelectronic device, the method comprising:
   providing a semiconductor chip, wherein the semiconductor chip is configured to emit a primary radiation during operation of the device;
   producing a conversion element, the conversion element comprising a conversion material which comprises Cr and/or Ni ions and a host material, wherein the host material comprises $Ln_3Ga_5GeO_{14}$ and $Ga_2O_3$,
   wherein Ln=La, Ce, Pr, Nd, Pm, Sm, Eu, Gd, Tb, Dy, Ho, Er, Tm, Yb and/or Lu, and
   applying the conversion element over the semiconductor chip, wherein the conversion element is configured to convert, during operation of the device, the primary radiation emitted by the semiconductor chip into secondary radiation of a wavelength between 700 nm and 2000 nm.

15. The method according to claim 14, wherein producing the conversion element comprises mixing starting materials and calcining the mixed starting material at a temperature between 700° C. and 1500° C. to form the conversion material.

16. The method according to claim 15, wherein the starting materials are selected from metal oxides, metal hydroxides, metal carbonates, metal nitrates, metal halides, metal acetates, metal nitrides or combinations thereof.

* * * * *